(12) United States Patent
Tropello et al.

(10) Patent No.: US 11,612,546 B2
(45) Date of Patent: Mar. 28, 2023

(54) SYSTEMS, APPARATUS, AND METHODS FOR PLACING A GUIDEWIRE FOR A GASTROSTOMY TUBE

(71) Applicant: CoapTech, Inc., Baltimore, MD (US)

(72) Inventors: Steven P. Tropello, Baltimore, MD (US); Howard Carolan, Baltimore, MD (US); Elisabeth Goldwasser, Baltimore, MD (US)

(73) Assignee: CoapTech, Inc., Baltimore, MD (US)

( * ) Notice: Subject to any disclaimer, the term of this patent is extended or adjusted under 35 U.S.C. 154(b) by 0 days.

(21) Appl. No.: 17/080,441

(22) Filed: Oct. 26, 2020

(65) Prior Publication Data

US 2021/0244624 A1 Aug. 12, 2021

Related U.S. Application Data

(63) Continuation of application No. PCT/US2019/029351, filed on Apr. 26, 2019.
(Continued)

(51) Int. Cl.
*A61J 15/00* (2006.01)
*A61B 17/34* (2006.01)
*A61B 90/00* (2016.01)

(52) U.S. Cl.
CPC ....... *A61J 15/0019* (2013.01); *A61B 17/3403* (2013.01); *A61B 17/3468* (2013.01);
(Continued)

(58) Field of Classification Search
CPC ............ A61J 15/0019; A61B 17/3403; A61B 17/3468; A61B 2017/3413;
(Continued)

(56) References Cited

U.S. PATENT DOCUMENTS 3,961,632 A 6/1976 Moosun
4,403,612 A 9/1983 Fogarty
(Continued)

FOREIGN PATENT DOCUMENTS

EP 0 371 486 A1 6/1990
IT MI20111820 A1 4/2013
(Continued)

OTHER PUBLICATIONS

International Search Report and Written Opinion issued by the International Examining Authority for Application No. PCT/US2021/038263, dated Oct. 14, 2021, 10 pages.
(Continued)

*Primary Examiner* — Brooke Labranche
(74) *Attorney, Agent, or Firm* — Cooley LLP

(57) ABSTRACT

Devices, systems, and methods for guidewire placement for a gastrostomy tube are described herein. A system can include an elongated tube, an inflatable member, and a guidewire assembly. The elongated tube can have a first end, a second end, and can define a lumen. The inflatable member can be coupled to the first end of the elongated tube and can be fluidically coupled to the lumen such that the inflatable member can receive fluid via the lumen. The guidewire assembly can include a guidewire having a first end and a second end. The first end of the guidewire assembly can include a coupling member, the coupling member configured to couple to the inflatable member such that translation of the elongated tube translates the guidewire assembly.

20 Claims, 24 Drawing Sheets

Related U.S. Application Data

(60) Provisional application No. 62/663,766, filed on Apr. 27, 2018.

(52) U.S. Cl.
CPC .............. *A61B 2017/3413* (2013.01); *A61B 2017/3486* (2013.01); *A61B 2090/376* (2016.02)

(58) Field of Classification Search
CPC ..... A61B 2017/3486; A61B 2090/376; A61M 2025/09125; A61M 2025/09175; A61M 25/09

See application file for complete search history.

(56) References Cited

U.S. PATENT DOCUMENTS

| | | |
|---|---|---|
| 5,058,580 A | 10/1991 | Hazard |
| 5,112,310 A | 5/1992 | Grobe |
| 5,154,387 A | 10/1992 | Trailer |
| 5,265,622 A | 11/1993 | Barbere |
| 5,431,640 A | 7/1995 | Gabriel |
| 5,458,583 A | 10/1995 | McNeely et al. |
| 5,497,782 A | 3/1996 | Fugoso |
| 5,653,230 A | 8/1997 | Ciagla et al. |
| 5,669,380 A | 9/1997 | Garry et al. |
| 5,681,260 A | 10/1997 | Ueda et al. |
| 6,015,414 A | 1/2000 | Werp et al. |
| 6,126,647 A | 10/2000 | Posey et al. |
| 6,173,199 B1 | 1/2001 | Gabriel |
| 6,651,665 B1 | 11/2003 | Sellers et al. |
| 6,685,671 B1 | 2/2004 | Oishi et al. |
| 6,701,918 B2 | 3/2004 | Fariss et al. |
| 6,702,804 B1 | 3/2004 | Ritter et al. |
| 7,761,133 B2 | 7/2010 | Viswanathan et al. |
| 7,769,428 B2 | 8/2010 | Viswanathan et al. |
| 7,853,306 B2 | 12/2010 | Viswanathan et al. |
| 7,963,910 B2 | 6/2011 | Okada |
| 8,226,637 B2 | 7/2012 | Satake |
| 8,419,681 B2 | 4/2013 | Sell |
| 8,677,990 B2 | 3/2014 | Gabriel |
| 8,764,769 B1 | 7/2014 | Rodriguez-Navarro et al. |
| 8,790,245 B2 | 7/2014 | Rodriguez Fernandez et al. |
| 8,834,370 B2 | 9/2014 | Evert et al. |
| 8,997,748 B2 | 4/2015 | Margolin et al. |
| 10,219,778 B2 | 3/2019 | Tropello |
| 10,383,595 B2 | 8/2019 | Tropello |
| 2002/0055757 A1 | 5/2002 | Torre et al. |
| 2003/0040671 A1 | 2/2003 | Somogyi et al. |
| 2004/0255954 A1 | 12/2004 | Zgoda et al. |
| 2006/0009735 A1 | 1/2006 | Viswanathan et al. |
| 2006/0025675 A1 | 2/2006 | Viswanathan et al. |
| 2006/0025676 A1 | 2/2006 | Viswanathan et al. |
| 2006/0025719 A1 | 2/2006 | Viswanathan et al. |
| 2006/0247530 A1 | 11/2006 | Hardin, Jr. et al. |
| 2007/0135825 A1 | 6/2007 | Binmoeller |
| 2007/0205785 A1 | 9/2007 | Nilsson |
| 2008/0045863 A1 | 2/2008 | Bakos |
| 2008/0194994 A1 | 8/2008 | Bown et al. |
| 2008/0294102 A1 | 11/2008 | Cartledge et al. |
| 2009/0012517 A1 | 1/2009 | De la Rama et al. |
| 2009/0062772 A1 | 3/2009 | Wakeford et al. |
| 2009/0198153 A1 | 8/2009 | Shriver |
| 2010/0094116 A1 | 4/2010 | Silverstein |
| 2010/0145147 A1 | 6/2010 | Pinsky et al. |
| 2010/0179510 A1 | 7/2010 | Fox et al. |
| 2012/0143029 A1 | 6/2012 | Silverstein et al. |
| 2012/0197062 A1 | 8/2012 | Requarth |
| 2012/0203175 A1 | 8/2012 | Sun |
| 2012/0265130 A1 | 10/2012 | De la Rama |
| 2013/0047993 A1 | 2/2013 | Lally |
| 2013/0053770 A1 | 2/2013 | Aggerholm et al. |
| 2013/0072792 A1 | 3/2013 | Aggerholm et al. |
| 2014/0039358 A1 | 2/2014 | Zhou et al. |
| 2014/0180242 A1 | 6/2014 | Tai |
| 2014/0180252 A1 | 6/2014 | Gabriel |
| 2014/0200504 A1 | 7/2014 | Rocha-Singh |
| 2014/0228680 A1 | 8/2014 | Fukuda |
| 2014/0276941 A1 | 9/2014 | Rodriguez-Navarro et al. |
| 2015/0045615 A1 | 2/2015 | Bates et al. |
| 2016/0081652 A1 | 3/2016 | Tropello |
| 2016/0279393 A1 | 9/2016 | Anderson et al. |
| 2016/0302811 A1 | 10/2016 | Rodriguez-Navarro et al. |
| 2018/0078234 A1 | 3/2018 | Tropello |
| 2019/0167298 A1 | 6/2019 | Tropello |
| 2020/0214661 A1 | 7/2020 | Tropello |

FOREIGN PATENT DOCUMENTS

| | | |
|---|---|---|
| JP | H6-503243 A | 4/1994 |
| JP | H8-89583 A | 4/1996 |
| JP | H08-117232 A | 5/1996 |
| JP | H11-56852 A | 3/1999 |
| JP | 2003-93332 A | 4/2003 |
| JP | 2004-283606 A | 10/2004 |
| JP | 3806601 | 8/2006 |
| JP | 2008-284136 A | 11/2008 |
| JP | 2012-501689 A | 1/2012 |
| JP | 2012-502749 | 2/2012 |
| JP | 2013-121390 | 6/2013 |
| WO | WO-99/36120 | 7/1999 |
| WO | WO-2006/005012 A2 | 1/2006 |
| WO | WO-2006/005012 A3 | 1/2006 |
| WO | WO-2010-033629 A1 | 3/2010 |
| WO | WO-2010/036721 A2 | 4/2010 |
| WO | WO-2010/036721 A3 | 4/2010 |
| WO | WO-2010/129327 A1 | 11/2010 |
| WO | WO-2012/003665 A1 | 1/2012 |
| WO | WO-2014/176236 A1 | 10/2014 |
| WO | WO-2017/176881 A1 | 10/2017 |
| WO | WO 2017/216650 A1 | 12/2017 |
| WO | WO-2019/210170 A1 | 10/2019 |
| WO | WO-2019/213657 A1 | 11/2019 |
| WO | WO-2019/232398 A1 | 12/2019 |

OTHER PUBLICATIONS

Office Action issued by the Japanese Patent Office for Application No. 2019-238125, dated Sep. 14, 2021, 8 pages (including 4 page English translation).

Park et al., "Simple and Safe Foley Catheter-Guided Tracheostomy Tube Changes," Trauma Image Proced, 2018(2): 72-75.

Extended European Search Report issued by the European Patent Office for Application No. 19797039.5, dated Jan. 4, 2022, 7 pages.

Extended European Search Report issued by the European Patent Office for Application No. 19793773.3, dated Feb. 2, 2022, 7 pages.

Extended European Search Report issued by the European Patent Office for Application No. 19811977.8, dated Feb. 9, 2022, 7 pages.

International Search Report and Written Opinion issued by the International Examining Authority for Application No. PCT/US2014/034950, dated Oct. 1, 2014, 8 pages.

International Search Report and Written Opinion issued by the International Examining Authority for Application No. PCT/US2017/026141, dated Aug. 25, 2017, 11 pages.

International Search Report and Written Opinion issued by the International Examining Authority for Application No. PCT/US2019/029351, dated Jul. 17, 2019, 9 pages.

International Search Report and Written Opinion issued by the International Examining Authority for Application No. PCT/US2019/030902, dated Jul. 18, 2019, 7 pages.

International Search Report and Written Opinion issued by the International Examining Authority for Application No. PCT/US2019/034943, dated Aug. 27, 2019, 7 pages.

Extended European Search Report issued by the European Patent Office for U.S. Appl. No. 14/788,472, dated Dec. 21, 2016, 7 pages.

Arias, Elizabeth, et al. "United States Life Tables, 2005." National Vital Stat Reports. vol. 58, No. 10., Mar. 2010.

Arora, Gaurav, et al. Percutaneous Endoscopic Gastrostomy (PEG) Tube Placement. Dec. 27, 2012. Updated Dec. 14, 2015. http://emedicine.medscape.com/article/149665-overview.

(56) References Cited

OTHER PUBLICATIONS

Duszak, Richard, et al. "Percutaneous Gastrostomy and Jejunostomy." Dec. 27, 2012. Updated Jan. 14, 2014. http://emedicine.medscape.com/article/1821257-overview.

Gauderer, Michael W. L. "Percutaneous endoscopic gastrostomy-20 years later: a historical perspective." Journal o Pediatric Surgery, 2001; 36: 217-219.

Lohsiriwat, Varul. "Percutaneous endoscopic gastrostomy tube replacement: A simple procedure?" World Journal of Gastrointestinal Endoscopy, Jan. 16, 2013; 5: 14-18.

Lynch, C.R. and J.C. Fang. "Prevention and Management of Complications of PEG tubes." Practical 3astroenterology, Nov. 2004; 66-76.

Rosenberger, Laura H., et al. "Late accidental dislodgement of a percutaneous endoscopic gastrostomy tube: an underestimated burden on patients and the health care system." Surgical Endoscopy, Oct. 2011; 25: 3307-3311.

Tsukuda, Toshinobu, et al. "Percutaneous Radiologic Gastrostomy Using Push-Type Gastrostomy Tubes with CT and Fluoroscopic Guidance." Interventional Radiology, Feb. 2006; 186: 574-576.

Office Action issued by the Japanese Patent Office for Application No. 2016-510734, dated Jan. 30, 2018, 12 pages (including 6 page English translation).

Office Action issued by the United States Patent and Trademark Office for U.S. Appl. No. 14/785,366, dated Jun. 13, 2018, 12 pages.

Office Action issued by the United States Patent and Trademark Office for U.S. Appl. No. 14/785,366, dated Jan. 11, 2019, 11 pages.

Notice of Allowance issued by the United States Patent and Trademark Office for U.S. Appl. No. 14/785,366 dated May 13, 2019, 8 pages.

Office Action issued by the United States Patent and Trademark Office for U.S. Appl. No. 15/809,665 dated Jun. 14, 2018, 8 pages.

Notice of Allowance issued by the United States Patent and Trademark Office for U.S. Appl. No. 15/809,665 dated Nov. 29, 2018, 7 pages.

Office Action issued by the Japanese Patent Office for Application No. 2016-510734, dated Dec. 11, 2018, 10 pages (including 5 page English translation).

Extended European Search Report issued by the European Patent Office for Application No. 18177361.5, dated Jan. 23, 2019, 8 pages.

Office Action issued by the Japanese Patent Office for Application No. 2019-238125, dated Jan. 12, 2021, 4 pages.

Office Action issued by the Chinese Patent Office for Application No. 201980040162.9, dated Jul. 29, 2022, 8 pages (including 10 page English translation).

SYSTEMS, APPARATUS, AND METHODS FOR PLACING A GUIDEWIRE FOR A GASTROSTOMY TUBE

CROSS-REFERENCE TO RELATED APPLICATIONS

This application is a continuation of International PCT Application No. PCT/US2019/029351, filed Apr. 26, 2019, entitled "Systems, Apparatus, and Methods for Placing a Guidewire for a Gastrostomy Tube," which claims priority to and the benefit of U.S. Provisional Application No. 62/663,766, filed Apr. 27, 2018, entitled "Systems, Apparatus, and Methods for Placing a Guidewire for a Gastrostomy Tube," the entire contents of each of which are hereby expressly incorporated by reference for all purposes.

BACKGROUND

Embodiments described herein relate to systems, apparatus, and methods for placing a guidewire for a gastrostomy tube to provide access to a patient's stomach via a route bypassing the esophagus of the patient.

Some patients suffer from medical conditions that impair the patient's ability to swallow food and liquids. Such medical conditions can include, for example, cancer, coma, stroke, diabetes, Crohn's disease, neurological disorders, and HIV. Gastrostomy tubes (also referred to as "G-tubes") can be used to provide a path for nutrition delivery directly into the stomach of a patient, bypassing the mouth and esophagus of the patient. In the United States, approximately 250,000 gastrostomy tubes are placed annually. Some methods of placing a gastrostomy tube include creating incisions through an abdominal wall and a stomach wall of a patient and securing a gastrostomy tube within the incisions such that one end of the tube is disposed in the stomach and the second end is disposed outside of the patient. The creation of incisions, however, can cause harmful bleeding and is associated with the risk of accidentally perforating an organ. Thus, highly-skilled specialists such as gastroenterologists (e.g., using endoscopy) or interventional radiologists (e.g., via percutaneous radiologic gastrostomy using imaging modalities such as fluoroscopy or computerized tomography) are often needed to place gastrostomy tubes.

Thus, there is a need for systems, apparatus, and methods of placing a gastrostomy tube which reduce risks to the patient and allow for the gastrostomy tube to be quickly and easily placed and secured in communication with the stomach.

SUMMARY

Systems, apparatus, and methods for placing a guidewire for a gastrostomy tube are described herein. In some embodiments, a system includes an elongated tube, an inflatable member, and a guidewire assembly. The elongated tube can have a first end, a second end, and can define a lumen. The inflatable member can be coupled to the first end of the elongated tube and can be fluidically coupled to the lumen such that the inflatable member can receive fluid via the lumen. The guidewire assembly can include a guidewire having a first end and a second end. The first end of the guidewire assembly can include a coupling member, the coupling member configured to couple to the inflatable member such that translation of the elongated tube translates the guidewire assembly.

DETAILED DESCRIPTION

In some embodiments, a system includes an elongated tube, an inflatable member, and a guidewire assembly. The elongated tube can have a first end, a second end, and can define a lumen. The inflatable member can be coupled to the first end of the elongated tube and can be fluidically coupled to the lumen such that the inflatable member can receive fluid via the lumen. The guidewire assembly can include a guidewire having a first end and a second end. The first end of the guidewire assembly can include a coupling member, the coupling member configured to couple to the inflatable member such that translation of the elongated tube translates the guidewire assembly.

In some embodiments, a method can include translating an inflatable member of an elongated tube through an orifice of a patient, through an esophagus of the patient, and into a stomach of the patient. The inflatable member can then be inflated via a lumen of the elongated tube such that the inflatable member transitions from an uninflated configuration to an inflated configuration. A coupling member of a guidewire assembly can be translated through a stomach wall of the stomach. The guidewire assembly can include a guidewire having a first end coupled to the coupling member and a second end disposed outside the patient, the guidewire extending through the stomach wall. The coupling member can be coupled to the inflatable member. The elongated tube can be withdrawn through the orifice such that the coupling member and the first end of the guidewire are withdrawn from the orifice and such that the guidewire extends through the esophagus, stomach, and stomach wall of the patient and the second end of the guidewire is disposed outside of the patient.

In some embodiments, a method can include translating an inflatable member of an elongated tube through an orifice of a patient and to a first location within the patient. The inflatable member can then be inflated via a lumen of the elongated tube such that the inflatable member transitions from an uninflated configuration to an inflated configuration. A coupling member of a guidewire assembly can be translated through a tissue wall of the patient to a second location within the patient near the first location. The guidewire assembly can include a guidewire having a first end coupled to the coupling member and a second end disposed outside the patient. The guidewire can extend through the tissue wall when the coupling member is disposed in the second location. The coupling member can then be coupled to the inflatable member. The elongated tube can then be withdrawn through the orifice such that the coupling member and the first end of the guidewire are withdrawn from the orifice and such that the guidewire extends through the orifice, the first location, and the tissue wall of the patient and the second end of the guidewire is disposed outside of the patient.

Figure 1:
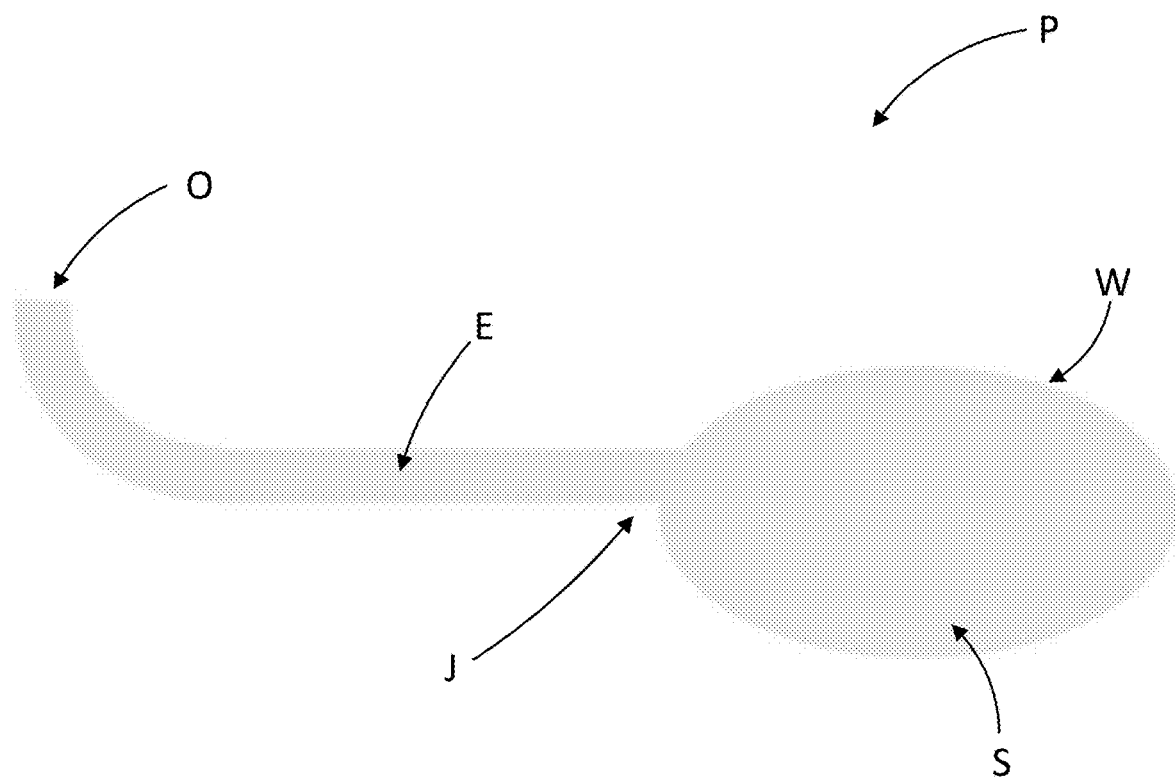
FIG. 1 is a schematic illustration of a portion of a patient, according to an embodiment.

FIG. 1 is a schematic illustration of a portion of a patient P. The patient P has an orifice O, an esophagus E, and a stomach S. The orifice O can be, for example, an oral orifice or a nasal orifice. The orifice O is coupled to the esophagus E and the esophagus E is coupled to the stomach S at the gastroesophageal junction J. Thus, the stomach S is accessible from the orifice O via the esophagus E. The stomach S includes a stomach wall W such that the interior of the stomach S can be accessed via piercing the stomach wall W.

When the patient P has difficulty swallowing food and/or liquid, a gastrostomy tube can be placed via a gastrostomy tract created in the stomach wall W such that nutrition can be provided directly through the gastrostomy tube to the stomach. For example, the stomach wall W can be serially dilated to create the gastrostomy tract. External serial dilation of the gastrostomy tract, however, is time-intensive. As another example of gastrostomy placement, a first end of a stiff catheter can be fluoroscopically directed through a preformed gastrostomy tract in the stomach wall W, through the stomach S, and through the esophagus E to the gastroesophageal junction J. After the first end of the stiff catheter has been translated through the gastroesophageal junction J, a guidewire can be translated through the catheter, out of the first end of the catheter, and through the orifice O of the patient. A gastrostomy tube can then be translated over the guidewire and secured in the gastrostomy tract in engagement with the stomach wall W. For example, the gastrostomy tube can be pushed over the guidewire from the orifice O, through the esophagus E, into the stomach S, and into engagement with the stomach wall W. Alternatively, the gastrostomy tube can be coupled to the first end of the guidewire (e.g., a looped end) extending from the orifice O and pulled through the orifice O, through the esophagus E, into the stomach S, and into engagement with the stomach wall W by the guidewire. Navigation of the catheter and the guidewire through the patient, however, can be challenging and pose risks to the patient. For example, the extended use of fluoroscopy to navigate the stiff catheter through the patient carries the risk of radiation-induced injuries to the patient. Furthermore, if internal guidance (e.g., fluoroscopy) is not used to navigate the catheter and guidewire through the patient, the catheter may need to be stiffer to traverse the route through the patient. Catheters with increased stiffness, however, are more likely to damage tissue via unintended tears and/or perforations.

Figure 2:
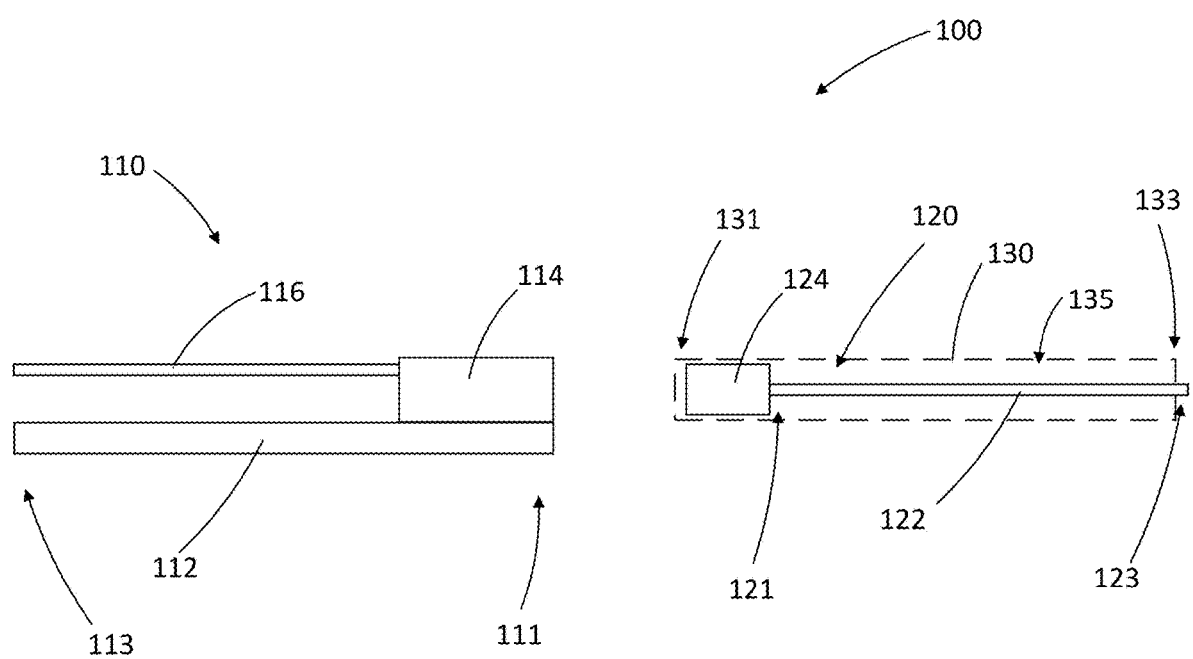
FIG. 2 is a schematic illustration of a guidewire placement system, according to an embodiment.

In some embodiments, however, a guidewire can be inserted through a stomach wall of a patient and coupled to an elongated tube within the stomach such that the guidewire can be pulled through the esophagus and orifice (e.g., nasal or oral) of a patient. For example, FIG. 2 is a schematic representation of a system 100. The system 100 includes an inflation assembly 110 and a guidewire assembly 120. The inflation assembly 110 can include an elongated tube 112 and an inflatable member 114. The elongated tube 112 can have a first end 111 and a second end 113. In some embodiments, the elongated tube 112 can have a length sufficient to extend from at least an oral or nasal orifice of a patient to the stomach of a patient via an esophagus of the patient. The inflatable member 114 can be coupled to the elongated tube 112 at or near the first end 111 of the elongated tube 112. The inflation assembly 110 can include an inflation lumen 116 in fluid communication with the inflatable member 114. In some embodiments, the inflation lumen 116 can be disposed within and/or be defined by the elongated tube 112.

In some embodiments, the inflatable member 114 can surround the elongated tube 112 in an inflated and/or uninflated configuration. In some embodiments, the inflatable member 114 can extend laterally from the elongated tube 112 in an inflated and/or uninflated configuration. In some embodiments, the inflatable member 114 can extend distally from the first end 111 of the elongated tube 112 in an inflated and/or uninflated configuration. In some embodiments, the inflatable member 114 can be disposed on the elongated tube 112 such that a portion of the elongated tube 112 extends distally of the inflatable member 114 when the inflatable member 114 is in an inflated and/or uninflated configuration. In some embodiments, the inflatable member 114 can have two ends (e.g., cuffs), and each end can be sealed to an outer surface of the elongated tube 112. The elongated tube 112 can define one or more inflation holes such that the inflation lumen 116 can be in fluid communication with the interior of the inflatable member 114 for transitioning the inflatable member 114 between an uninflated and an inflated configuration. In some embodiments, the inflatable member 114 can be formed on or as a part of a rigid subassembly, and the rigid subassembly can receive the elongated tube 112 within an orifice of the subassembly and the elongated tube 112 can then be sealed to the subassembly.

In some embodiments, the inflatable member 114 can be formed in any suitable shape, in any suitable size, and of any suitable material. For example, the inflatable member 114 can be elliptical, spherical, cylindrical, rectangular, tear drop, or any other suitable shape. In some embodiments, the shape can be chosen based on the particular application of the system 100. For example, the shape of the inflatable member 114 may be selected to improve ultrasound visualization in particular regions of a patient's body. Furthermore, the inflatable member 114 can be sized for improved engagement and retention between the inflatable member 114 and the guidewire assembly 120.

The inflatable member 114 can be sufficiently pliable such that the inflatable member 114 (e.g., when inflated) can be punctured (e.g., by a needle) to define a pinhole in the wall of the inflatable member 114 rather than bursting or tearing as a result of puncture. In some embodiments, the inflatable member 114 can be formed of, for example, polyurethane, silicone, and/or polyvinyl chloride (PVC). In some embodiments, the inflatable member 114 can have any suitable material properties, wall thicknesses, and/or inflated outermost diameters.

In some embodiments, for example, the inflatable member 114 can be elliptical in shape and formed of a low durometer urethane. The inflatable member 114 can have an outermost diameter ranging from about 40 mm to about 55 mm in an inflated configuration, and a length of about 55 mm. The inflatable member 114 can have a diameter at each end ranging from about 5.46 mm to about 5.72 mm. The wall thickness at the maximum balloon diameter in the inflated configuration can be between about 0.029 mm and about 0.038 mm. The inflatable member 114 can be filled with up to, for example, about 50 ml of fluid in the inflated configuration.

The guidewire assembly 120 can include a guidewire 122 having a first end 121 and a second end 123 and a coupling member 124 disposed at the first end 121 of the guidewire 122. The coupling member 124 can be configured to couple to the inflatable member 114 such that, when coupled, translation of the inflation assembly 110 (e.g., translation of the elongated tube 112 via pulling on the second end 113) can translate the guidewire assembly 120. For example, if the inflatable member 114 is moved in a first direction due to a force applied to the elongated tube 112, the coupling of the coupling member 124 to the inflatable member 114 can cause the coupling member 124 and the guidewire 122 to also move in the first direction. The coupling member 124 can be configured to couple with the inflatable member 114 via, for example, being captured by the inflatable member 114, caught within an interior region of the inflatable member, or engaged with a surface of the inflatable member 114.

In some embodiments, the coupling member 124 can be distinct from the guidewire 122 and fixedly coupled to the guidewire 122 (e.g., via adhesive). For example, in some embodiments, the coupling member 124 can include a first magnetic member configured to couple to a second magnetic member of the inflatable member 114.

In some embodiments, the guidewire 122 can include the coupling member 124. For example, the coupling member 124 can be monolithically formed with a shaft of the guidewire 122 such that the guidewire assembly 120 is a one piece structure. Similarly, in some embodiments, the coupling member 124 and the guidewire 122 can be formed of the same material or materials. In some embodiments, the coupling member 124 can be shaped such that the coupling member 124 can engage with at least one portion of a wall of the inflatable member 114. For example, the coupling member 124 can have a planar or a multi-planar shape and can be formed as a pigtail, hook, coil, or corkscrew-shaped end to the guidewire 122. Thus, in some embodiments, the first end 121 of the guidewire 122 can be retained within or near the inflatable member 122 by the coupling member 124 when the coupling member 124 is disposed within the inflatable member 114. In some embodiments, the coupling member 124 can be disposed outside of the inflatable member 114 with the guidewire 122 passing through a first wall portion and a second, oppositely disposed wall portion of the inflatable member 114 such that the guidewire 122 is retained by the inflatable member 114 due to the interaction between the coupling member 124 and the first wall portion of the inflatable member 114. In some embodiments, the coupling member 124 can be partially disposed within the inflatable member 114 and partially disposed outside of the inflatable member 114 such that the guidewire assembly 120 is coupled to the inflatable member 114 for translation of the guidewire assembly 120 via movement of the inflation assembly 110.

In some embodiments, the coupling member 124 can be configured to transition between a first configuration for insertion and a second configuration for retention or coupling. For example, the coupling member 124 can have a smaller lateral extent (e.g., outermost diameter) relative to a central axis of the guidewire 124 in the first configuration than in the second configuration such that the coupling member 124 can fit inside the lumen 135 of the needle 130 in the first configuration and can expand to retain the guidewire 124 relative to the inflatable member 114 in the second configuration. In some embodiments, the coupling member 124 can have a first shape in the first configuration and a second shape in the second configuration such that the coupling member 124 can travel through an opening in at least one sidewall of the inflatable member 114 in the first configuration and can engage a sidewall of the inflatable member 114 in the second configuration such that the coupling member 124 is retained by the inflatable member 114. In some embodiments, the coupling member 124 can be biased toward the second configuration such that, in the absence of external forces on the coupling member 124, the coupling member 124 will assume the second configuration. In some embodiments, in the first configuration the coupling member 124 can be elongated such that the coupling member is shaped as a straight wire. The second configuration can correspond to an unbiased shape or configuration of the coupling member (e.g., a pigtail, hook, coil, or corkscrew-shape). In some embodiments, the guidewire 122 and/or the coupling member 124 can be formed of a shape-memory material such as, for example, Nitinol.

In some embodiments, when the coupling member 124 is within the lumen 135 of the needle 130, the needle 130 can compress the coupling member 124 such that the coupling member is in the first configuration. Thus, the coupling member 124 can have a smaller lateral extent relative to a central axis of the guidewire 124 (e.g., outermost diameter) when disposed within the lumen 135 of the needle 130 than when not within the needle 130. In some embodiments, the lumen 135 and the coupling member 124 can be structured and sized such that the coupling member 124 can be straight or substantially straight within the lumen 135 of the needle 130. For example, the lumen 135 can have an inner diameter similar to an outer diameter of the coupling member 124 (e.g., an outer diameter of a wire forming the coupling member 124 portion of the guidewire assembly 120) such that the coupling member 124 can be laterally compressed to a shape with a smaller outer diameter and/or elongated within the lumen 135 of the needle 130. In some embodiments, the outer diameter of a wire forming the coupling member 124 and the inner diameter of the lumen 135 can be relatively sized such that the outer diameter of the wire forming the coupling member 124 is slightly smaller than the inner diameter of the lumen 135 and the coupling member 124 and the inner surface of the needle 130 defining the lumen 130 can have a slip fit engagement. Thus, when the coupling member 124 is threaded into the lumen 135 of the needle 130, the wire forming the coupling member 124 is straightened out to correspond to the shape of the lumen 135. As the coupling member 124 is translated out of the first end 131 of the needle 130, the coupling member 124 can transition from the first configuration to the second configuration. For example, as the coupling member 124 is extended from the first end 131 of the needle 130, the portion of the coupling member 124 extending from the first end 131 can transition toward the second configuration due to being biased toward the second configuration, while the portion of the coupling member 124 remaining within the lumen 135 of the needle 130 can remain in the first configuration. When the coupling member 124 is entirely outside of the needle 130, the coupling member 124 can be entirely in the second configuration.

In some embodiments, the coupling member 124 can be configured to be translated in a first direction by the inflatable member 114 if a translation force on the inflatable member 114 is greater than a force in a direction opposite of the translation force on the coupling member 124. If the force on the coupling member 124 is opposite and greater than the translation force on the inflatable member 114, the coupling member 124 and the inflatable member 114 can be configured to decouple. For example, in some embodiments in which the coupling member 124 is a pigtail-shaped end to the guidewire 122, the application of sufficient force to the coupling member 124 in a direction opposite a force being applied to the inflatable member 114 can cause the pigtail-shaped end to straighten and decouple from the inflatable member 114. Thus, in some embodiments the coupling member 124 and the inflatable member 114 can be decoupled via applying oppositely directing pulling forces to each of the coupling member 124 and the inflatable member 114. In some embodiments, the coupling member 124 and the inflatable member 114 can be engaged such that the release force (e.g., via oppositely directing pulling forces) necessary to separate the coupling member 124 from the inflatable member 114 is a force greater than the maximum force applied to the guidewire 122 (and therefore coupling member 124) in an opposite direction than the inflatable member 114 during withdrawal of the coupling member 124 from the patient via pulling on the inflation assembly 110. Thus, the release force is sufficiently high such that the inflatable member 114 and the coupling member 124 will not be separated during the withdrawal of the coupling member 124 of the guidewire 122 inadvertently during withdrawal, but can be separated via, for example, pulling by the user when the inflatable member 114 and the coupling member 124 are outside of the patient's body. For example, in some embodiments, the release force can be at least about 0.25 lbs of force, at least about 0.5 lbs of force, or at least about 1.5 lbs of force. In some applications of the system 100, such as non-gastrostomy applications, the release force may be greater or smaller depending on the resistive forces the coupling member 124 and guidewire 122 may experience during withdrawal via a withdrawal force on the inflation assembly 110.

In some embodiments, the coupling member 124 can be configured to pierce the inflatable member 114 such that the coupling member 124 can be inserted into and/or through the inflatable member 114. In some embodiments, the system 100 can optionally include a needle 130 having a first end 131, a second end 133, and defining a lumen 135. The first end 131 can have any suitable shape configured to pierce and create access to the inflatable member 114. For example, the first end 131 can have a sharpened tip that can be tapered. The lumen 135 can be sized such that the coupling member 124 of the guidewire assembly 120 can be translated through the second end 123, through the lumen 135, and through the first end 121 of the needle 130. In some embodiments, the needle 130 can be inserted through a stomach wall of the patient and through a sidewall of the inflatable member 114. The coupling member 124 and a portion of the guidewire 122 can then be translated through the lumen 135 of the needle 130 such that at least one of the coupling member 124 and a portion of the guidewire 122 is at least partially disposed within inflatable member 114. The needle 130 can then be removed from the inflatable member 114 via translating the needle 130 along the guidewire 122.

In some embodiments, the inflatable member 114 can be filled and/or inflated with a fluid (e.g., a liquid or a gaseous fluid) after being disposed in the stomach of the patient. For example, the inflatable member 114 can be filled and/or inflated with a fluid and/or contrast medium such that the inflatable member 114 defines an echogenic space detectable using ultrasound imaging. In some embodiments, the inflatable member 114 can be filled and/or inflated with a contrast medium such that the location of the inflatable member 114 can be visualized using fluoroscopy. Inflating the inflatable member 114 can also increase the surface tension of the sidewall of the inflatable member such that the needle 130 and/or the guidewire 122 can more easily pierce the sidewall. Further, inflation of the inflatable member 114 can create a larger interior space within which the coupling member 124 can expand and/or be disposed. Inflation of the inflatable member 114 can also increase the target size of the inflatable member for visualization and targeting of the inflatable member 114 with the needle 130 and/or coupling member 124.

In use, the inflation assembly 110 can be inserted through an orifice of a patient (e.g., a nose or mouth of a patient), through an esophagus of the patient, and into a stomach of the patient such that the inflation member 114 is disposed with the stomach of the patient and the elongated tube 112 extends from the inflation member 114 in the stomach, through the esophagus, and out of the orifice of the patient. Fluid can then be delivered to the inflatable member 114 via the inflation lumen 116. As described above, the fluid can include a fluid and/or contrast medium such that the inflatable member 114 is detectable via imaging (e.g., ultrasound or fluoroscopy). The inflatable member 114 can then be visualized such that the location of the inflatable member 114 can be identified.

While visualizing the location of the inflatable member 114, the guidewire assembly 120 can be inserted through a stomach wall of the stomach and coupled to the inflatable member 114. For example, the needle 130 can be inserted through the abdominal wall and stomach wall of the patient and through a sidewall of the inflatable member 114 such that the first end 131 of the needle 130 (e.g., the tip) is disposed within the inflatable member 114. The coupling member 124 and a portion of the guidewire 122 can be inserted through the lumen 135 of the needle 130 and translated (e.g., pushed) through the lumen 135. The coupling member 124 can then be translated out from the first end 131 of the needle 130 such that the coupling member 124 is disposed within the inflatable member 114. The needle 130 can then be withdrawn from the patient via translation of the needle 130 relative to the coupling member 124 and the guidewire 122, leaving the coupling member 124 within the inflatable member 114 and the guidewire 122 extending through a wall of the inflatable member 114. Additionally, the inflatable member 114 can be deflated in preparation for being withdrawn in tandem with the coupling member 124 through the esophagus.

The elongated tube 112 can then be translated (e.g., pulled) through the orifice of the patient such that the inflatable member 114 translates the coupling member 124 and the guidewire 122. For example, the elongated tube 112 can be translated relative to the orifice until the inflatable member 114, the coupling member 124, and the first end 121 of the guidewire 122 have been translated through the esophagus and out of the orifice and the guidewire extends from the first end 121, through the orifice, through the esophagus, into the stomach, and through the stomach wall to the second end 123 disposed outside of the patient. Thus, the first end 121 of the guidewire 122 can extend from the nose or mouth of the patient and be accessible near the patient's head, and the second end 123 of the guidewire 122 can extend from the stomach wall of the patient and be accessible near the patient's abdomen. A feeding tube (not shown) can then be pushed over the first end 121 of the guidewire 122 and translated along the guidewire 122 through the esophagus, into the stomach, and through the stomach wall until a portion of the feeding tube is disposed outside of the patient near or on the skin of the patient and a portion of the feeding tube is disposed within the patient's stomach. Then, the guidewire 122 can be removed from the patient via applying a retraction (e.g. pulling) force to the first end 121 of the guidewire 122 such that the second end 123 of the guidewire 122 is pulled through the stomach wall of the patient, through the stomach, through the esophagus, and out of the patient's oral or nasal orifice. Alternatively, the guidewire 122 can be removed from the patient via applying a retraction force to the second end 123 of the guidewire 122 such that the first end 121 of the guidewire 122 is pulled through the patient's oral or nasal orifice, through the esophagus, through the stomach, out of the stomach wall, and out of the skin of the patient. Thus, the feeding tube can provide direct access to the stomach of the patient such that food or liquid can be disposed in the stomach via the feeding tube without traversing the esophagus.

In some embodiments, rather than moving the coupling member 124 outside of the patient's body via the esophagus, the inflatable member 114 can be used to move the coupling member 124 to another region of the body (e.g., another region of the stomach or outside of the stomach).

Figure 3:
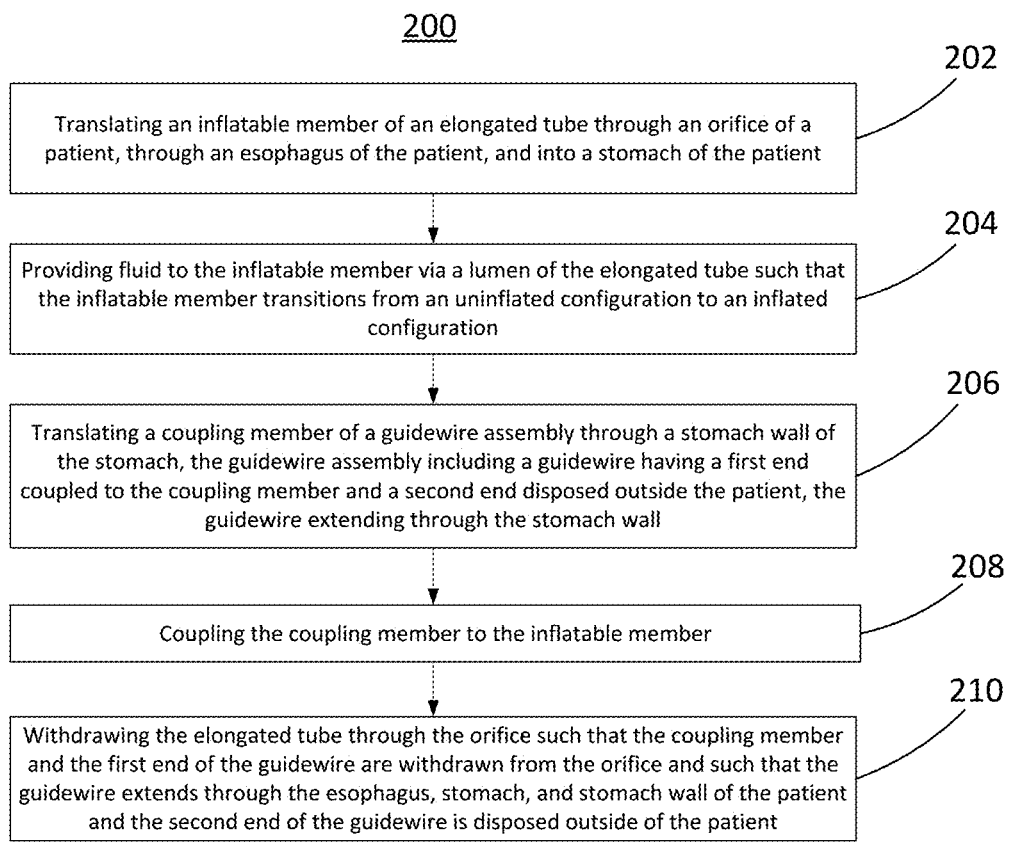
FIG. 3 is a flow chart of a method, according to an embodiment.

FIG. 3 is a flow chart of a method 200, according to an embodiment. The method 200 can be implemented using any of the systems or devices described herein, such as the system 100 described above. The method 200 includes translating 202 an inflatable member of an elongated tube through an orifice of a patient, through an esophagus of the patient, and into a stomach of the patient. Fluid (e.g., a liquid or a gaseous fluid) can be provided 204 to the inflatable member via a lumen of the elongated tube such that the inflatable member transitions from an uninflated configuration to an inflated configuration. In some embodiments, the fluid can include a contrast medium, and the method 200 can optionally include visualizing the location of the inflatable member via ultrasound or fluoroscopy. A coupling member of a guidewire assembly can be translated 206 through a stomach wall of the stomach. The guidewire assembly can include a guidewire having a first end coupled to the coupling member and a second end disposed outside the patient. The guidewire can extend through the stomach wall. In some embodiments, a needle can be inserted through the stomach wall of the stomach and through a sidewall of the inflatable member, and the coupling member of the guidewire assembly can be at least partially translated through a lumen of the needle.

The coupling member can be coupled 208 to the inflatable member. In some embodiments, the inflatable member can have a first sidewall portion and a second sidewall portion and the needle can be translated through both the first and second sidewall portions such that the coupling member of the guidewire assembly can be disposed outside of the inflatable member and the guidewire can pass through the first sidewall and the second sidewall such that the coupling member is coupled to the inflatable member. In some embodiments, the coupling member is configured to transition between a first configuration in which the coupling member is coiled and a second configuration in which the coupling member is straight, the coupling member being biased toward the first configuration. The coupling of the coupling member to the inflatable member can then include translating the coupling member distally of a distal end of the needle such that the coupling member at least partially transitions from the second configuration to the first configuration and withdrawing the needle relative to the coupling member such that the coupling member is retained in the stomach by the inflatable member.

The elongated tube can be withdrawn 210 through the orifice such that the coupling member and the first end of the guidewire are withdrawn from the orifice and such that the guidewire extends through the esophagus, stomach, and stomach wall of the patient and the second end of the guidewire is disposed outside of the patient.

Figure 4:
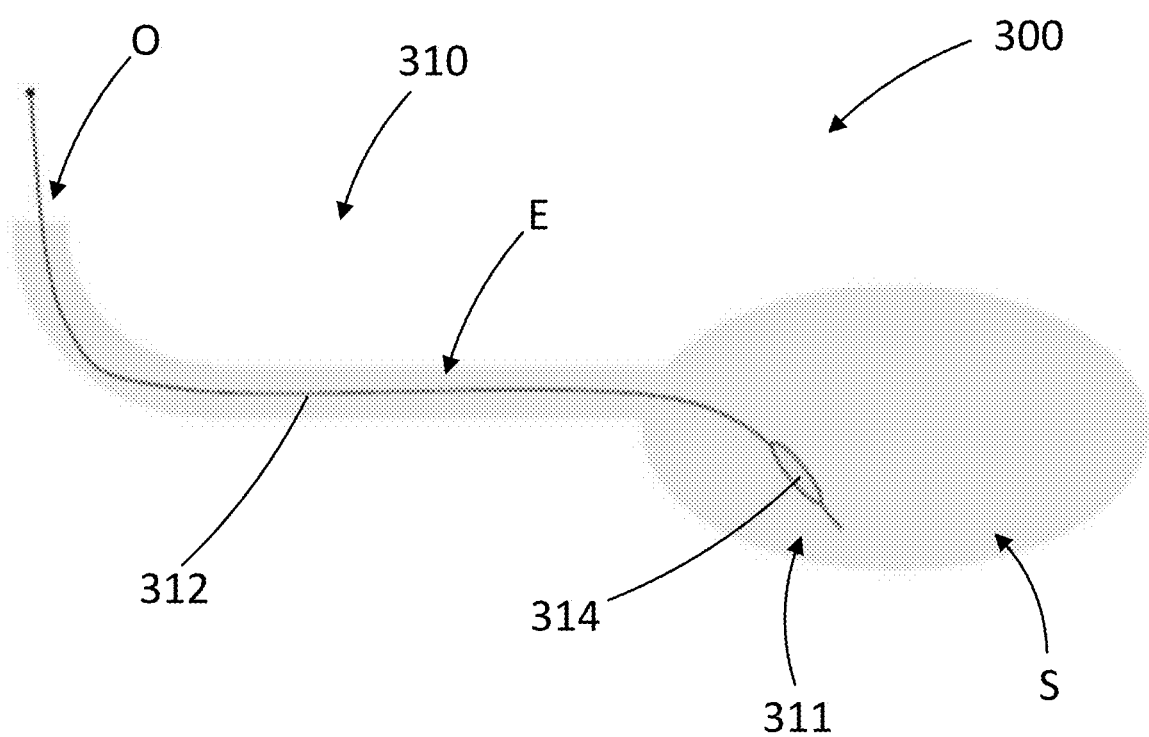
FIG. 4 is a schematic illustration of an inflation assembly of a system extended through the esophagus and stomach of a patient, according to an embodiment, in an uninflated configuration.

FIGS. 4-19 are schematic illustrations of a system 300 in various stages of operation. The system 300 can be the same or similar in structure and/or function to any of the systems or devices described herein, such as the system 100 described above. As shown in FIG. 4, an inflation assembly 310 can include an elongated tube 312 and an inflation member 314 disposed near a first end 311 of the elongated tube 312. A portion of the inflation assembly 310 can be inserted through an orifice O of a patient (e.g., a nose or mouth of a patient), through an esophagus E of the patient, and into a stomach S of the patient such that the inflation member 314 is disposed with the stomach S of the patient and the elongated tube 312 extends from the inflation member 314, through the esophagus E, and out of the orifice O of the patient.

Figure 5:
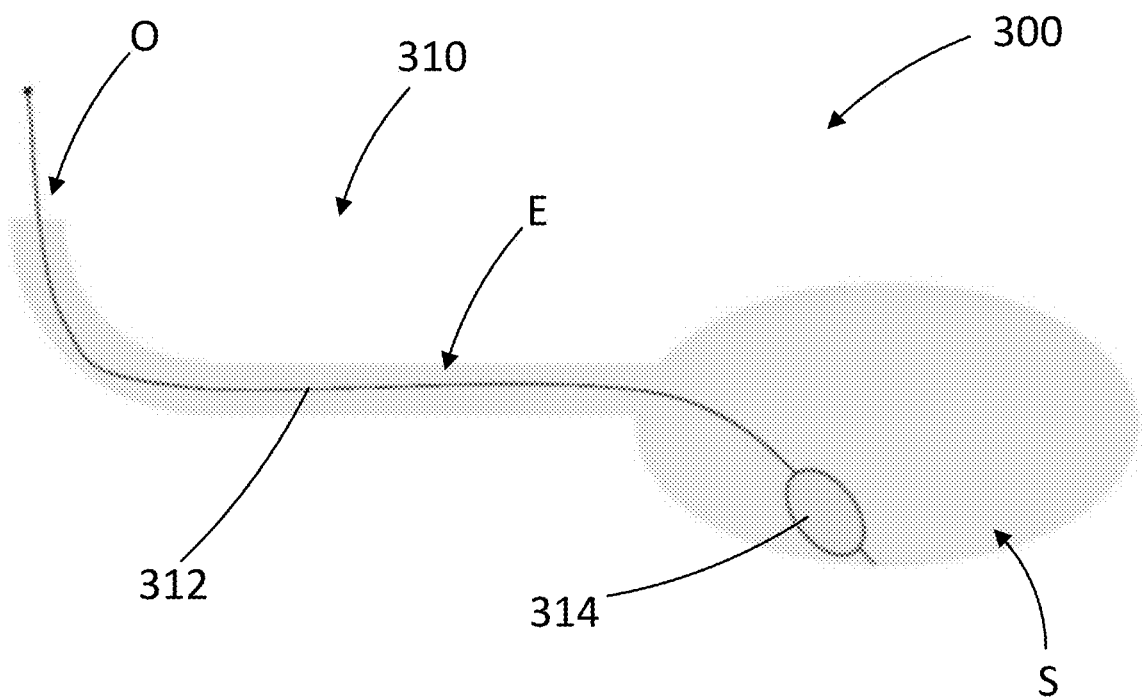
FIG. 5 is a schematic illustration of the system of FIG. 4 with the inflation assembly in an inflated configuration.

As shown in FIG. 5, fluid (e.g., a liquid or a gaseous fluid) can be delivered to the inflatable member 314 via an inflation lumen (not shown) of the elongated tube 312 such that the inflatable member 314 is filled and/or inflated. For example, the inflatable member 314 can be filled and/or inflated with a fluid and/or contrast medium such that the inflatable member 314 defines an echogenic space detectable using ultrasound imaging. In some embodiments, the inflatable member 314 can be filled and/or inflated with a contrast medium such that the location of the inflatable member 314 can be visualized using fluoroscopy. The inflatable member 314 can then be visualized using imaging (e.g., ultrasound or fluoroscopy) such that the location of the inflatable member 314 can be identified.

Figure 6:
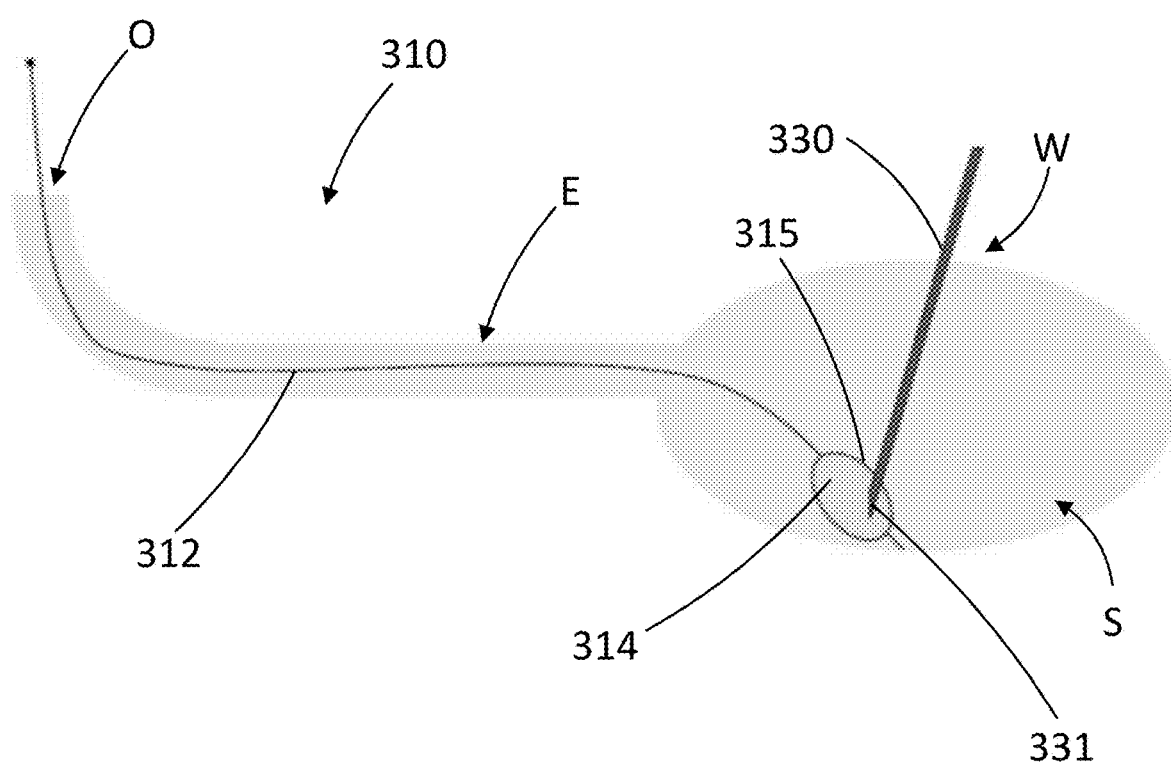
FIG. 6 is a schematic illustration of the system of FIG. 4 including a needle penetrating an inflatable member of the inflation assembly of FIG. 5.
Figure 7:
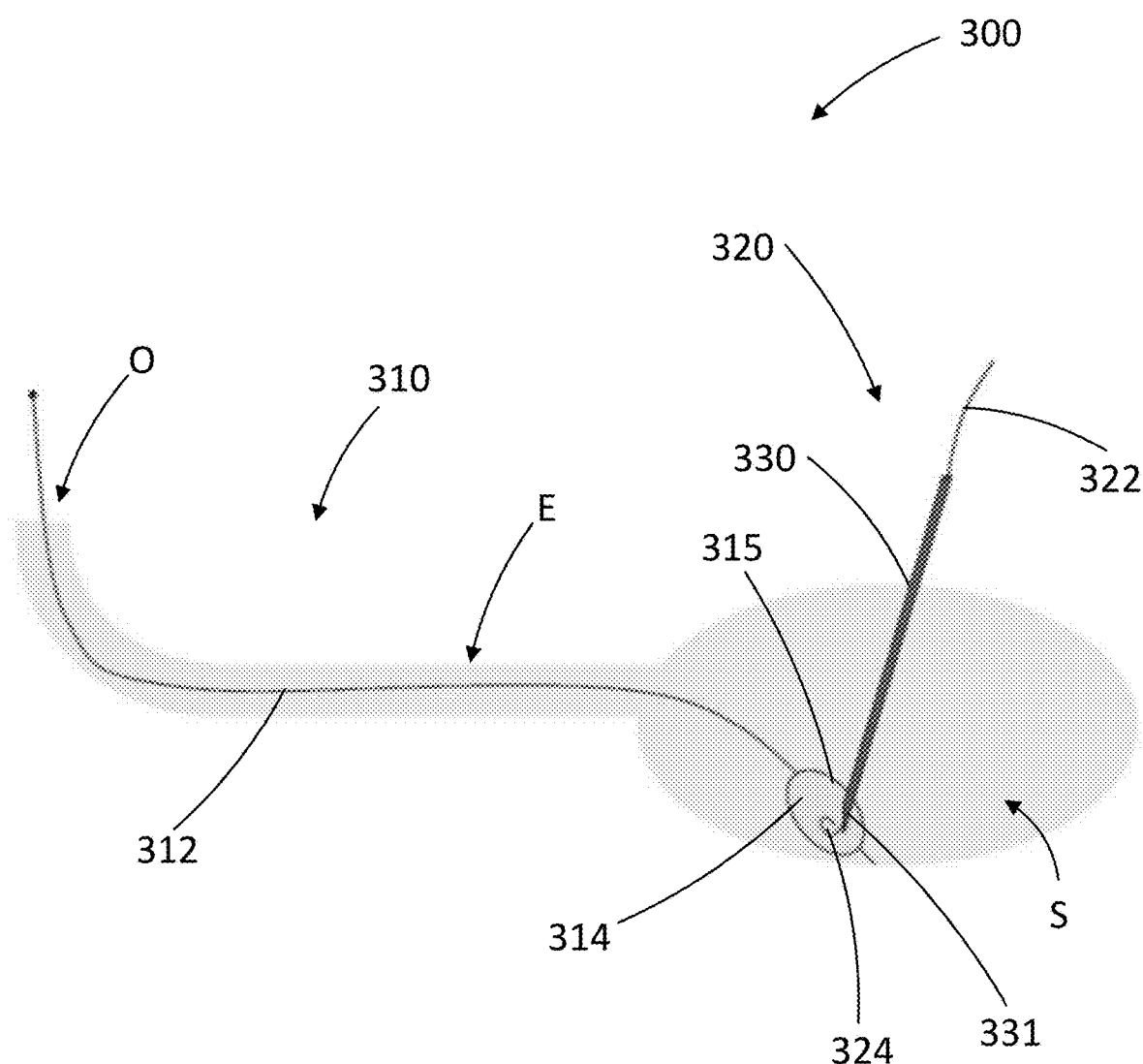
FIG. 7 is a schematic illustration of the system of FIG. 4 with a guidewire assembly extending through the needle into the inflatable member.

As shown in FIG. 6, a needle 330 can be inserted through the stomach wall W of the patient and through a sidewall portion 315 of the inflatable member 314 such that a first end 331 of the needle 330 (e.g., the tip) is disposed within the inflatable member 314. The needle 330 can be target toward and into engagement with the inflatable member using imaging (e.g., ultrasound or fluoroscopy). As shown in FIG. 7, a guidewire assembly 320 including a coupling member 324 and a guidewire 322 can be inserted through a lumen of the needle 330 and translated (e.g., pushed) through the lumen of the needle 330 until the coupling member 324 is disposed within the inflatable member 314. As shown in FIG. 7, the coupling member 324 can be configured to transition to a pigtail shape when extended from the first end 331 of the needle 330. Although shown as transitioning to a pigtail shape, the coupling member 324 can be configured to transition to any suitable shape, such as, for example, hook, coil, or corkscrew shapes.

Figure 8:
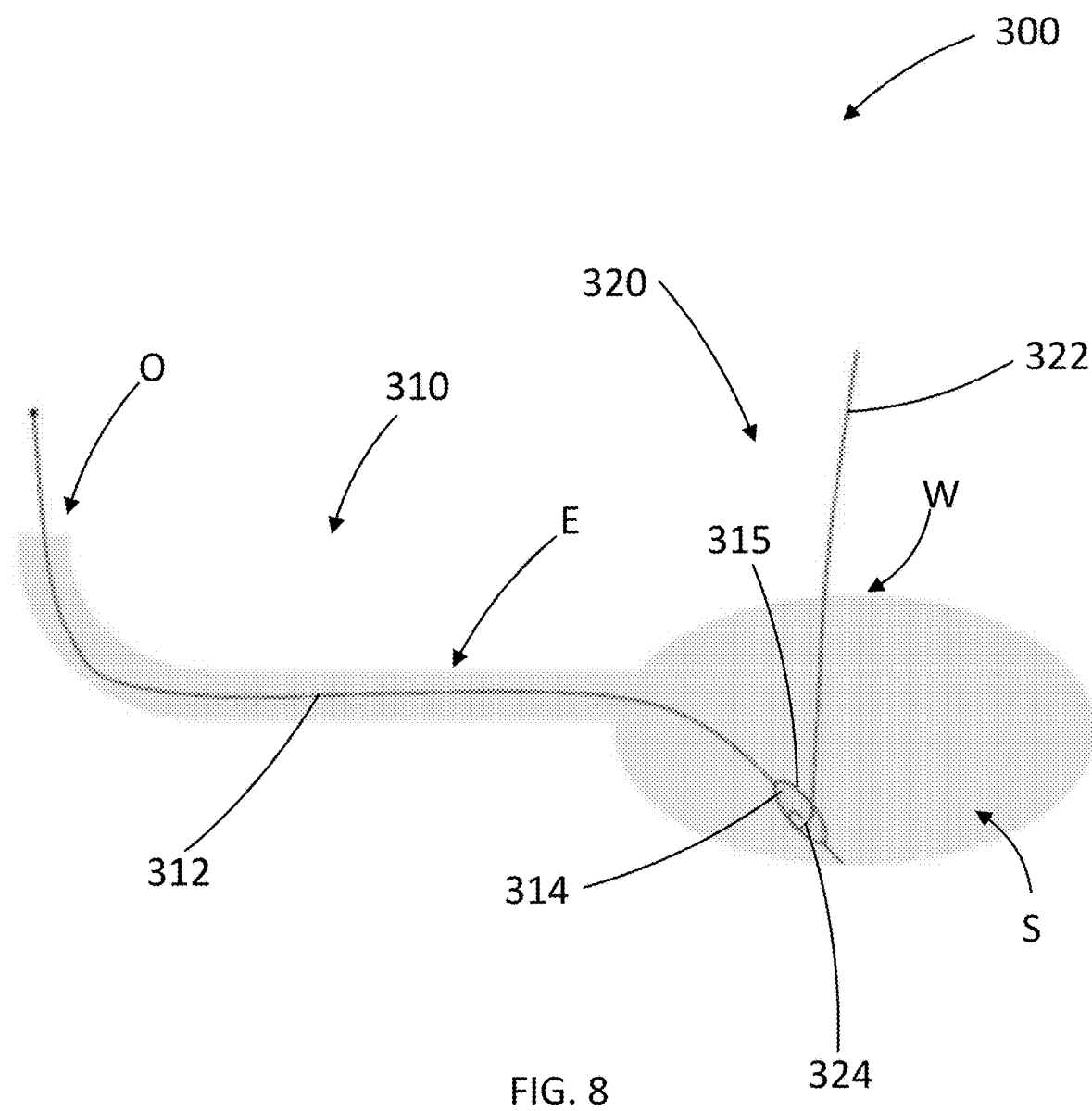
FIG. 8 is a schematic illustration of the system of FIG. 4 with the needle removed.

As shown in FIG. 8, the needle 330 can then be withdrawn from the patient via translation of the needle 330 relative to the coupling member 324 and the guidewire 322, leaving the coupling member 324 within the inflatable member 314 and the guidewire 322 extending through the wall portion 315 of the inflatable member 314. Additionally, the inflatable member 314 can be deflated in preparation for being withdrawn through the esophagus.

Figure 9:
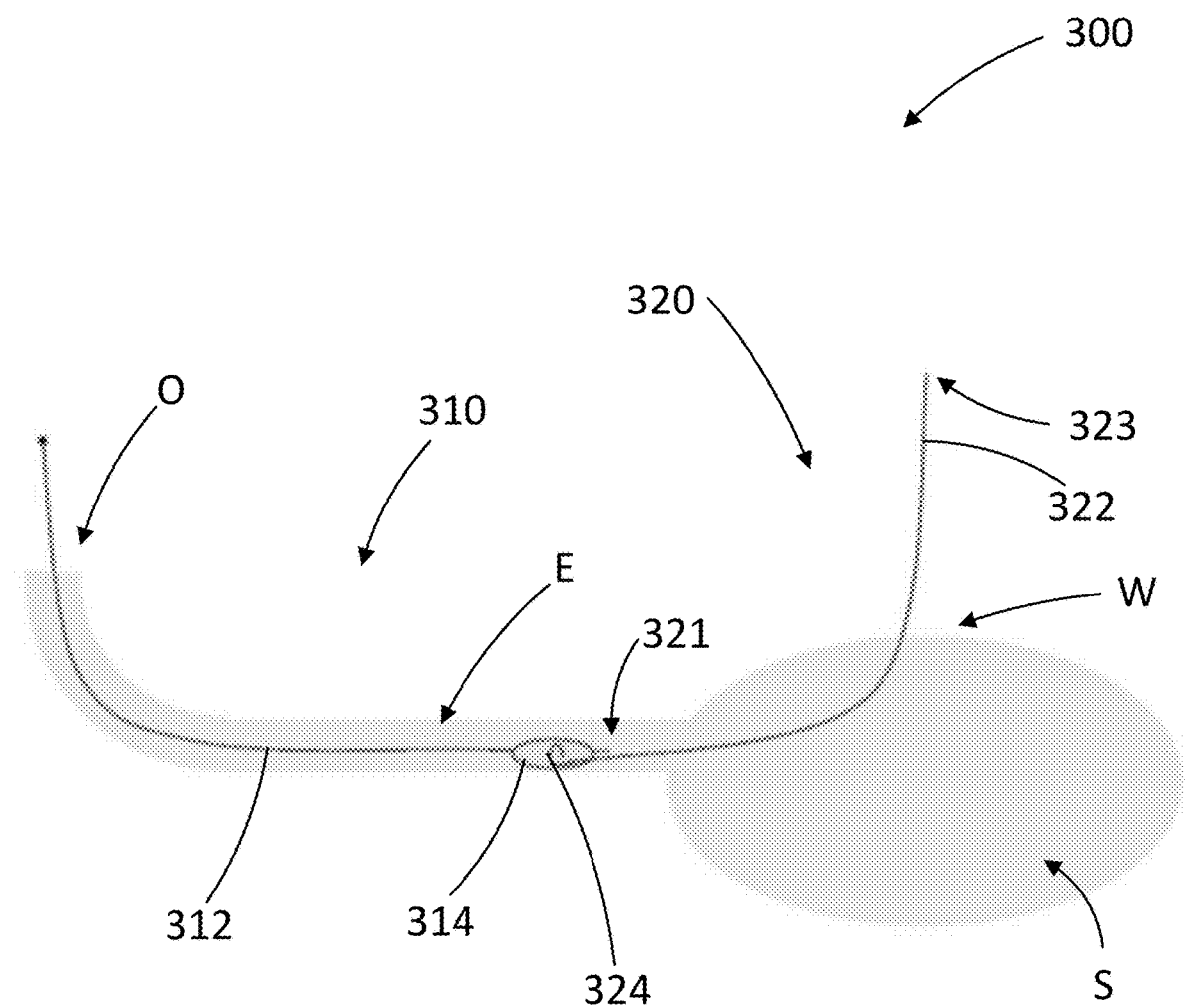
FIG. 9 is a schematic illustration of the system of FIG. 4 with the guidewire assembly partially pulled into the esophagus by the inflation assembly.
Figure 10:
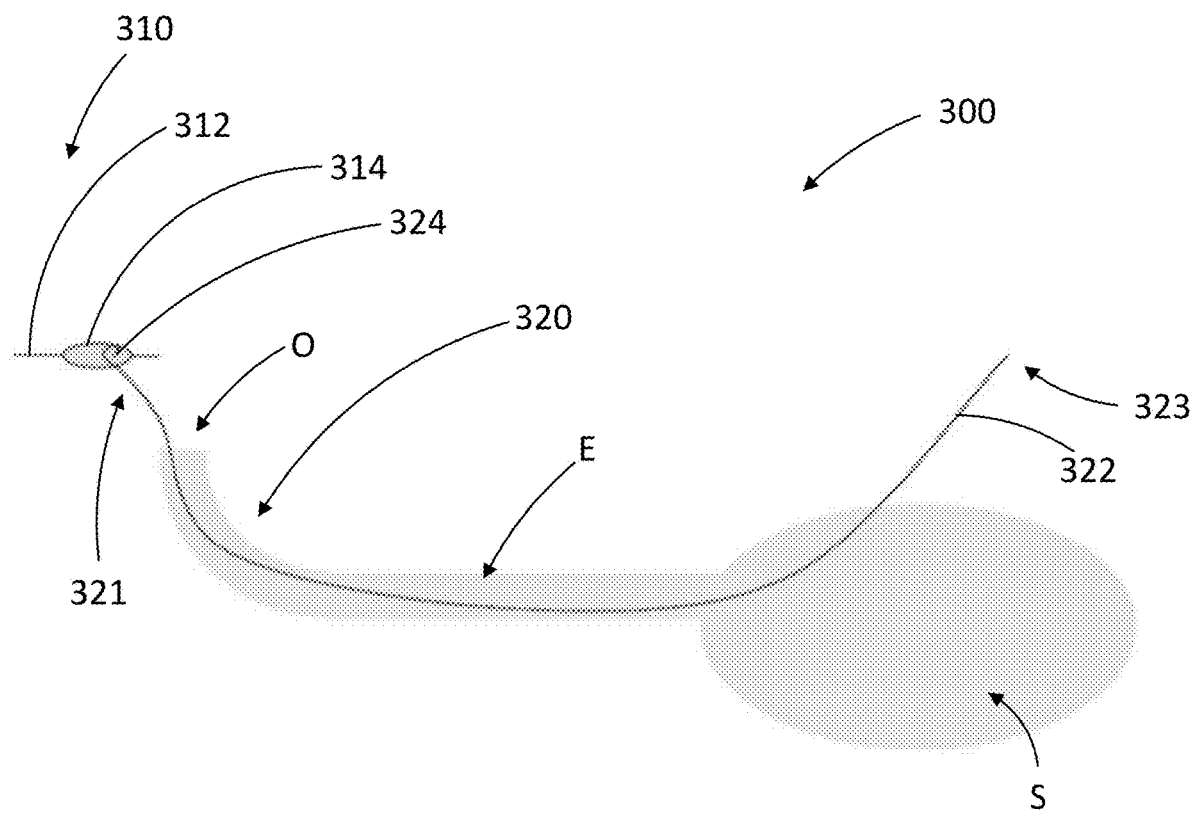
FIG. 10 is a schematic illustration of the system of FIG. 4 with the guidewire extending from the outside of the patient, through the orifice, through the esophagus, through the stomach, and outside the patient via an access opening.

As shown in FIGS. 9 and 10, the elongated tube 312 can then be translated (e.g., pulled) through the orifice O of the patient such that the inflatable member 314 translates the coupling member 324 and the guidewire 322 in tandem. For example, the elongated tube 312 can be translated relative to the orifice O until the inflatable member 314, the coupling member 324, and a first end 321 of the guidewire 322 have been translated through the esophagus E (as shown in FIG. 9) and out of the orifice O (as shown in FIG. 10), such that the guidewire 322 extends from the location of the coupling member 324 outside of the patient, through the orifice O, through the esophagus E, into the stomach S, and through the stomach wall W to a second end 323 of the guidewire 322 disposed outside of the patient. Thus, the first end 321 of the guidewire 322 can extend from the nose or mouth of the patient and be accessible near the patient's head, and the second end 323 of the guidewire 322 can extend through the stomach wall of the patient and be accessible near the patient's abdomen.

Figure 11:
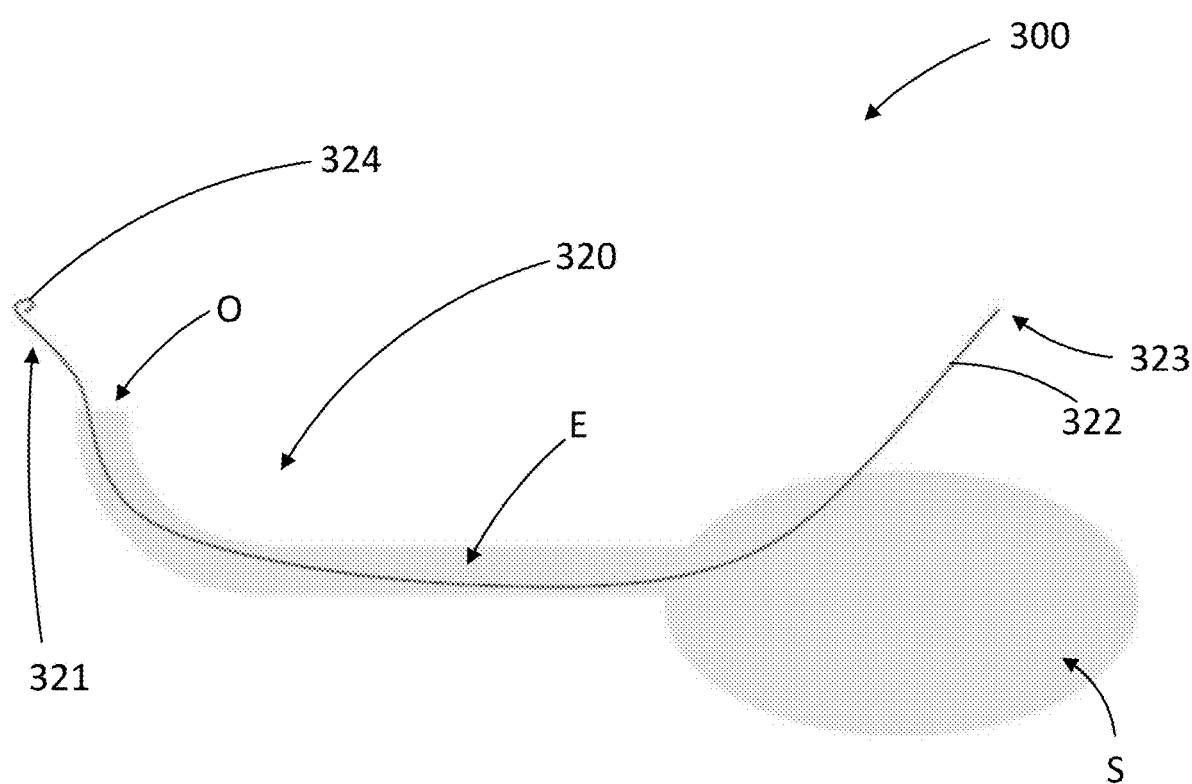
FIG. 11 is a schematic illustration of the system of FIG. 4 with the guidewire assembly separated from the inflation assembly.

As shown in FIG. 11, the inflatable member 314 can then, optionally, be decoupled from the coupling member 324 of the guidewire assembly 320. For example, a user can apply a first force on the inflatable member and a second force on the coupling member 324 in an opposite direction from the first force. The opposite forces can cause the pigtail-shaped coupling member 324 to straighten and decouple from the inflatable member 314 (e.g., slide out of the orifice created by the needle 330 within which the guidewire 322 is disposed).

Figure 12:
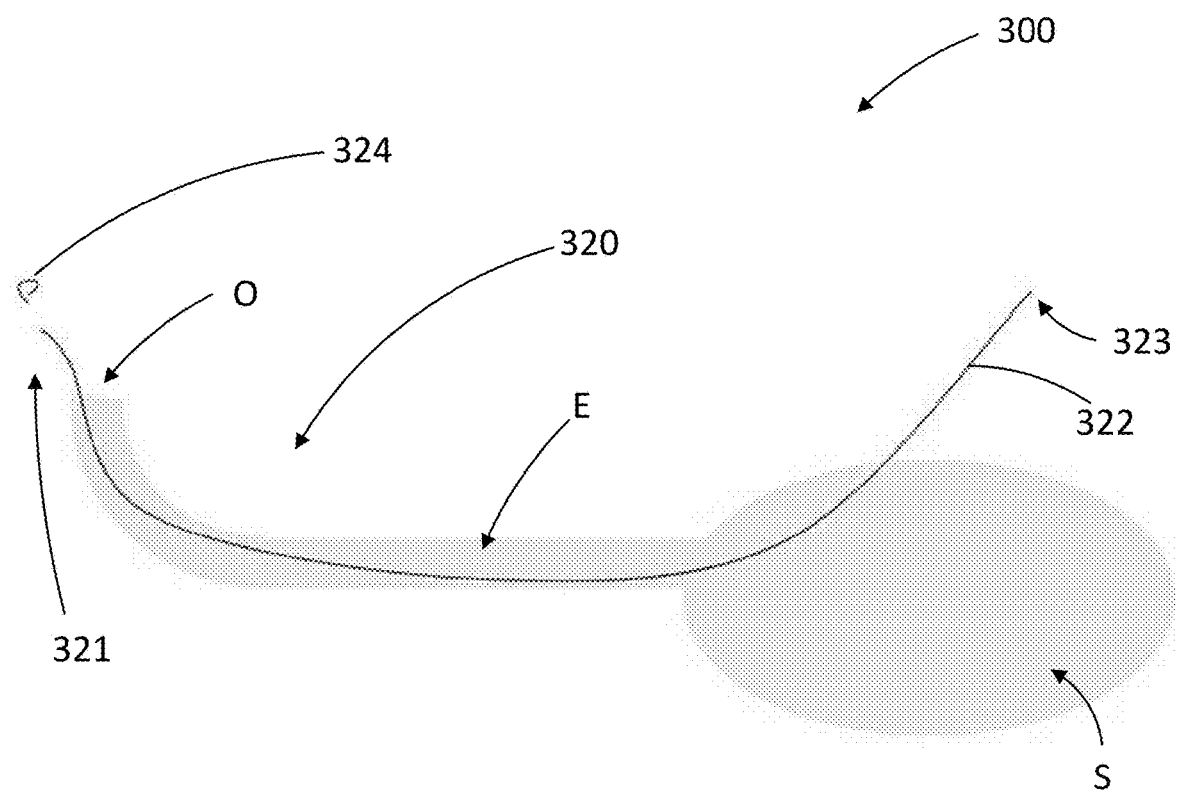
FIG. 12 is a schematic illustration of the system of FIG. 4 with a coupling member separated from the guidewire assembly.

As shown in FIG. 12, the coupling member 324 can be separated from the rest of the guidewire assembly 320 so that the coupling member 324 does not impede a feeding tube from being threaded along the guidewire 322. For example, the guidewire assembly 320 can be cut adjacent the coupling member 324 near the first end 321 of the guidewire 322 so that the coupling member 324 can be removed from the guidewire 322. The user can then dispose of the coupling member 324. In some embodiments, rather than decoupling the coupling member 324 from the guidewire assembly 320 prior to separating the coupling member 324 from the remainder of the guidewire assembly 320, the inflatable member 314 and the coupling member 324 can remain engaged during the separation of the coupling member 324 from the remainder of the guidewire assembly 320. The user can then dispose of the coupling member 324 and the inflatable member 314 simultaneously.

Figure 13:
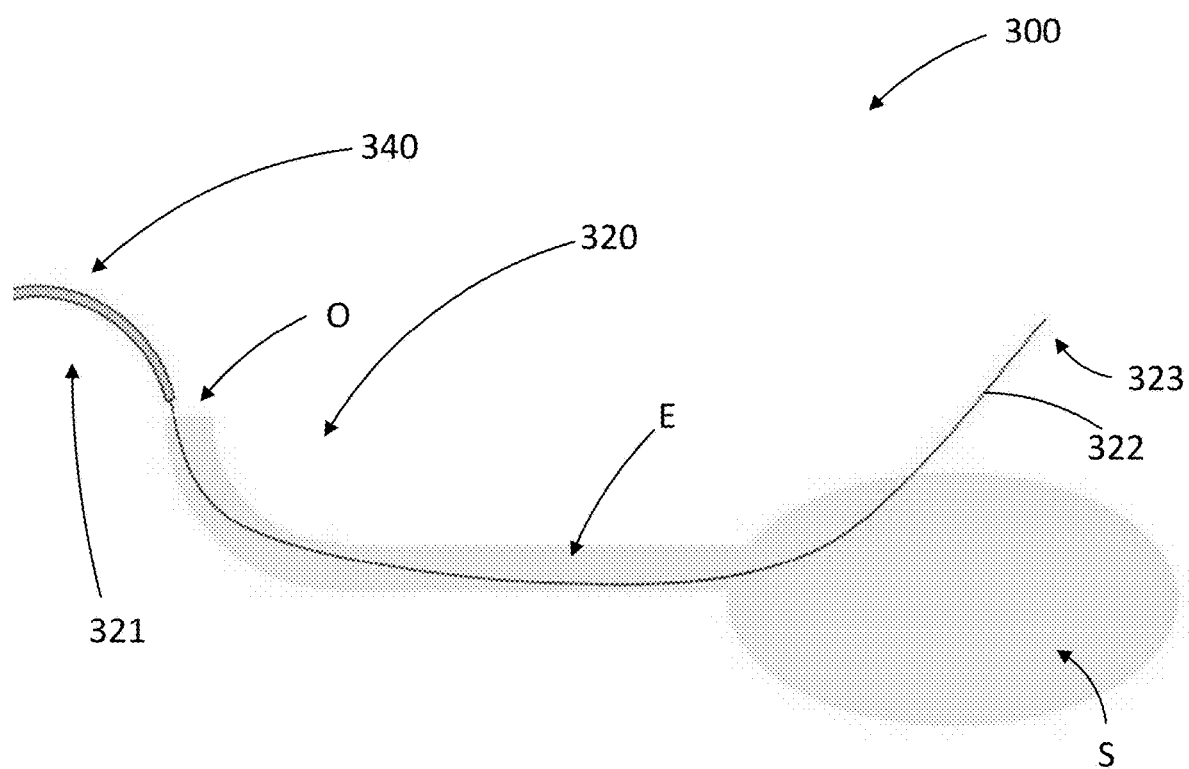
FIG. 13 is a schematic illustration of the system of FIG. 4 with a feeding tube threaded over the guidewire assembly.
Figure 14:
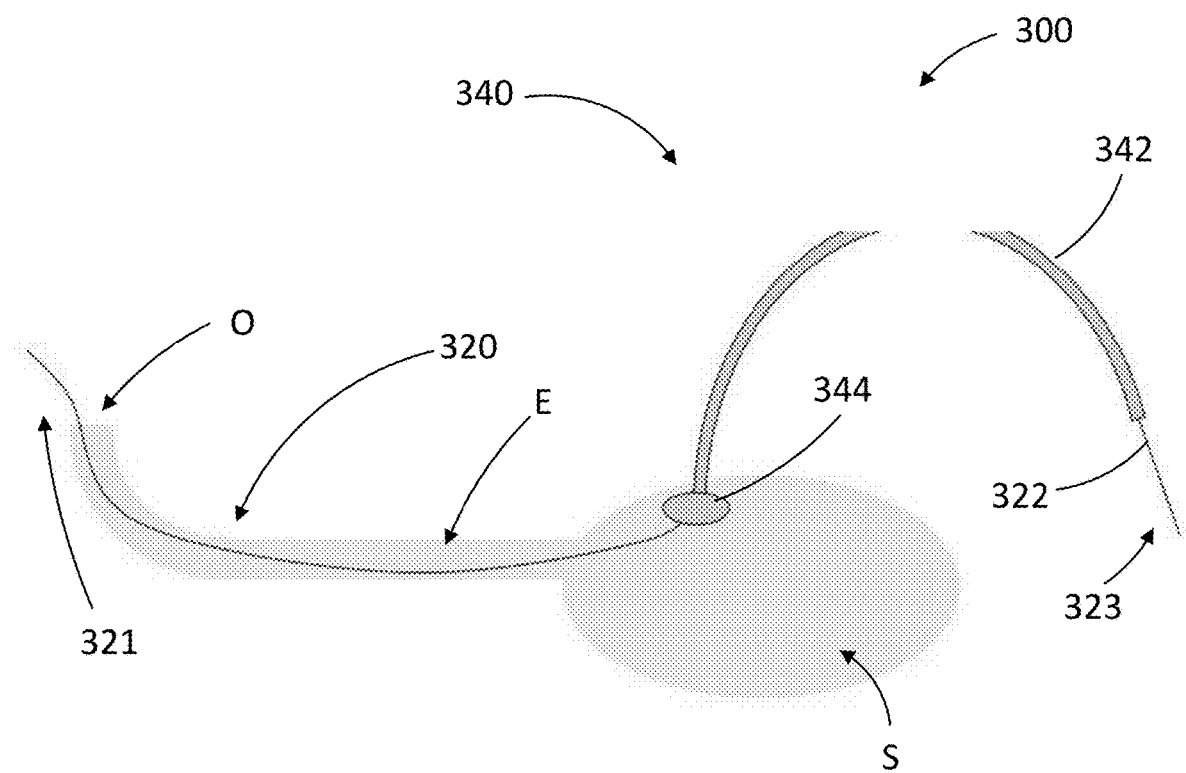
FIG. 14 is a schematic illustration of the system of FIG. 4 with the feeding tube engaged with the stomach wall and extending through the access opening in the stomach wall.

As shown in FIG. 13, a feeding tube 340 can then be pushed over the first end 321 of the guidewire 322 and translated along the guidewire 322 through the esophagus, into the stomach, and through the stomach wall until a portion of the feeding tube 340 is disposed outside of the patient near or on the skin of the patient and a portion of the feeding tube 340 is disposed within the patient's stomach. For example, as shown in FIG. 14, the feeding tube 340 can include a tube portion 342 and a retention portion 344. The retention portion 344 can be engaged with the inner wall of the patient's stomach and the tube portion 342 can extend through the patient's stomach wall and outside of the patient. The guidewire 322 can then be removed from the patient via applying a retraction (e.g. pulling) force to the first end 321 of the guidewire 322 such that the second end 323 of the guidewire 322 is pulled through the stomach wall of the patient, through the stomach, through the esophagus, and out of the patient's oral or nasal orifice, leaving the feeding tube 340 in place extending through the stomach wall. Alternatively, the guidewire 322 can be removed from the patient via applying a retraction force to the second end 323 of the guidewire 322 such that the first end 321 of the guidewire 322 is pulled through the patient's oral or nasal orifice, through the esophagus, through the stomach, out of the stomach wall, and out of the skin of the patient. Thus, the feeding tube 340 can provide direct access to the stomach of the patient such that food or liquid can be disposed in the stomach via the feeding tube 340 without traversing the esophagus.

Figure 15:
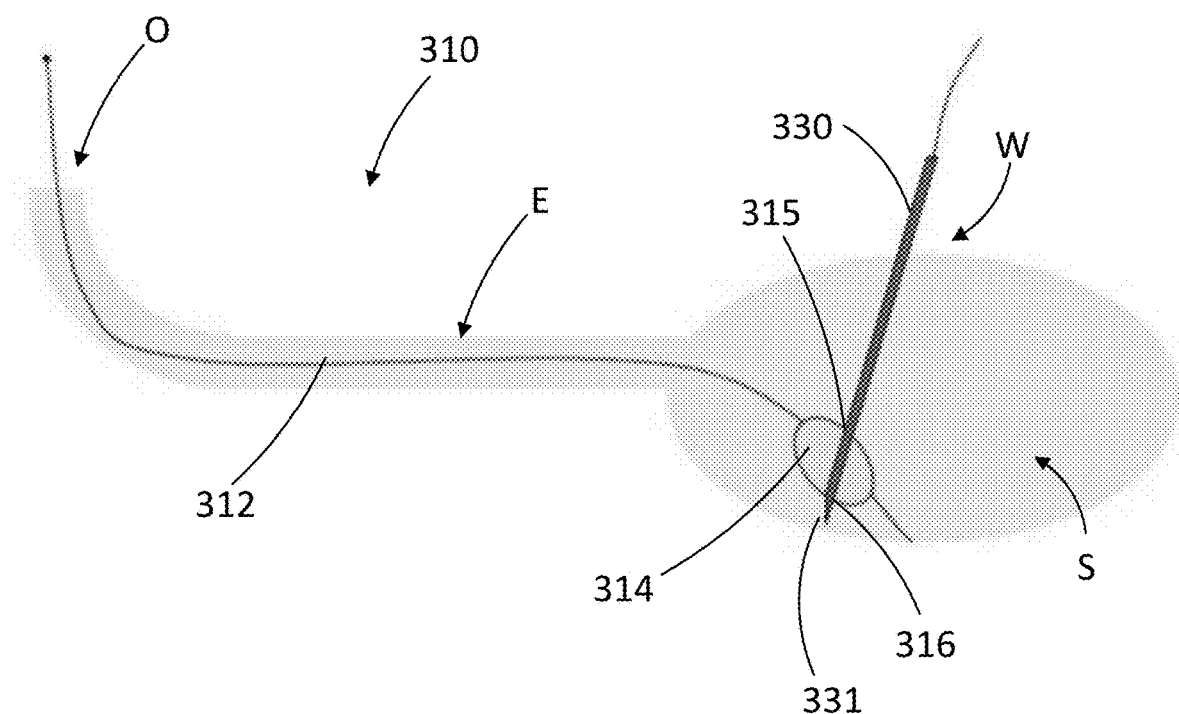
FIG. 15 is a schematic illustration of the system of FIG. 4, with the needle extending through the inflatable member, according to an alternative engagement method.
Figure 16:
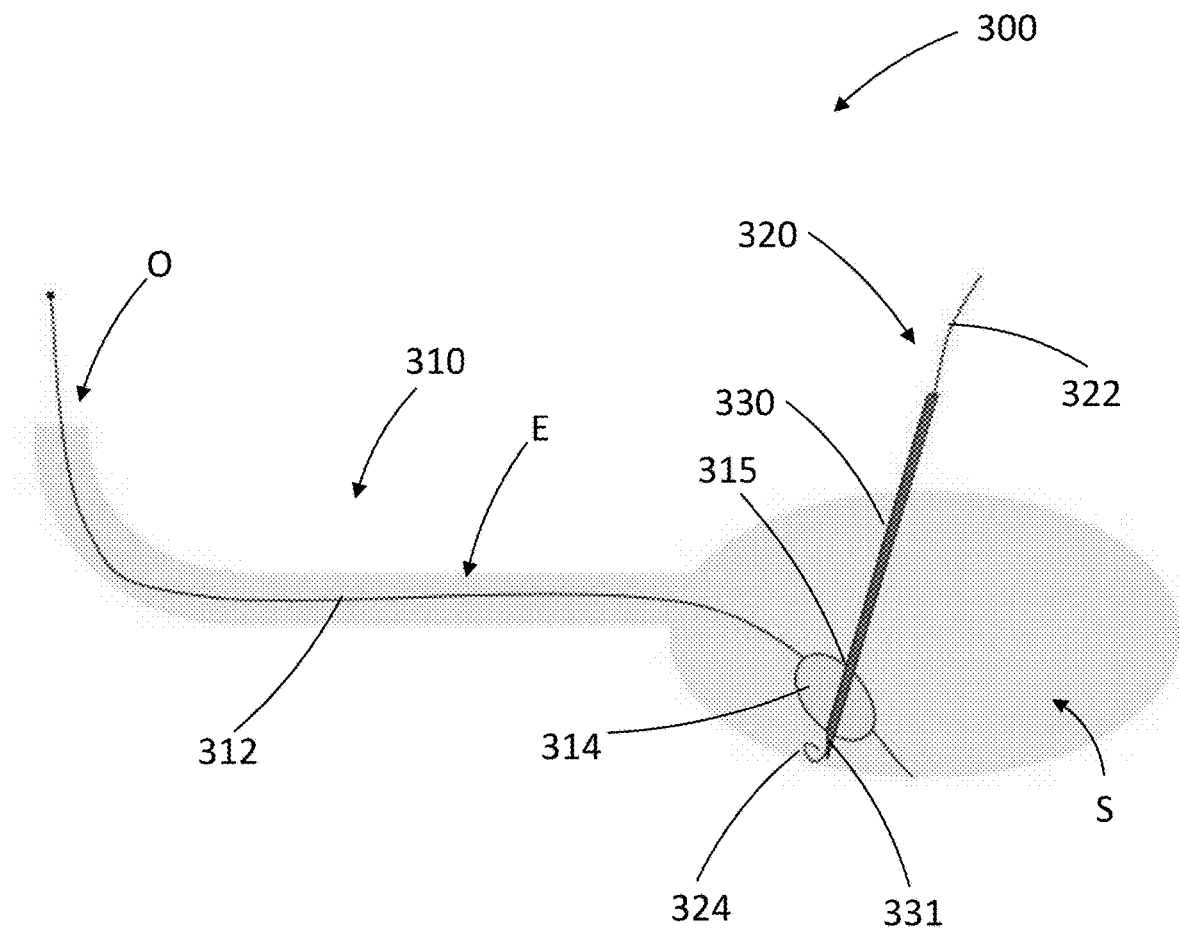
FIG. 16 is a schematic illustration of the system of FIG. 15, with the guidewire assembly threaded through the needle.
Figure 17:
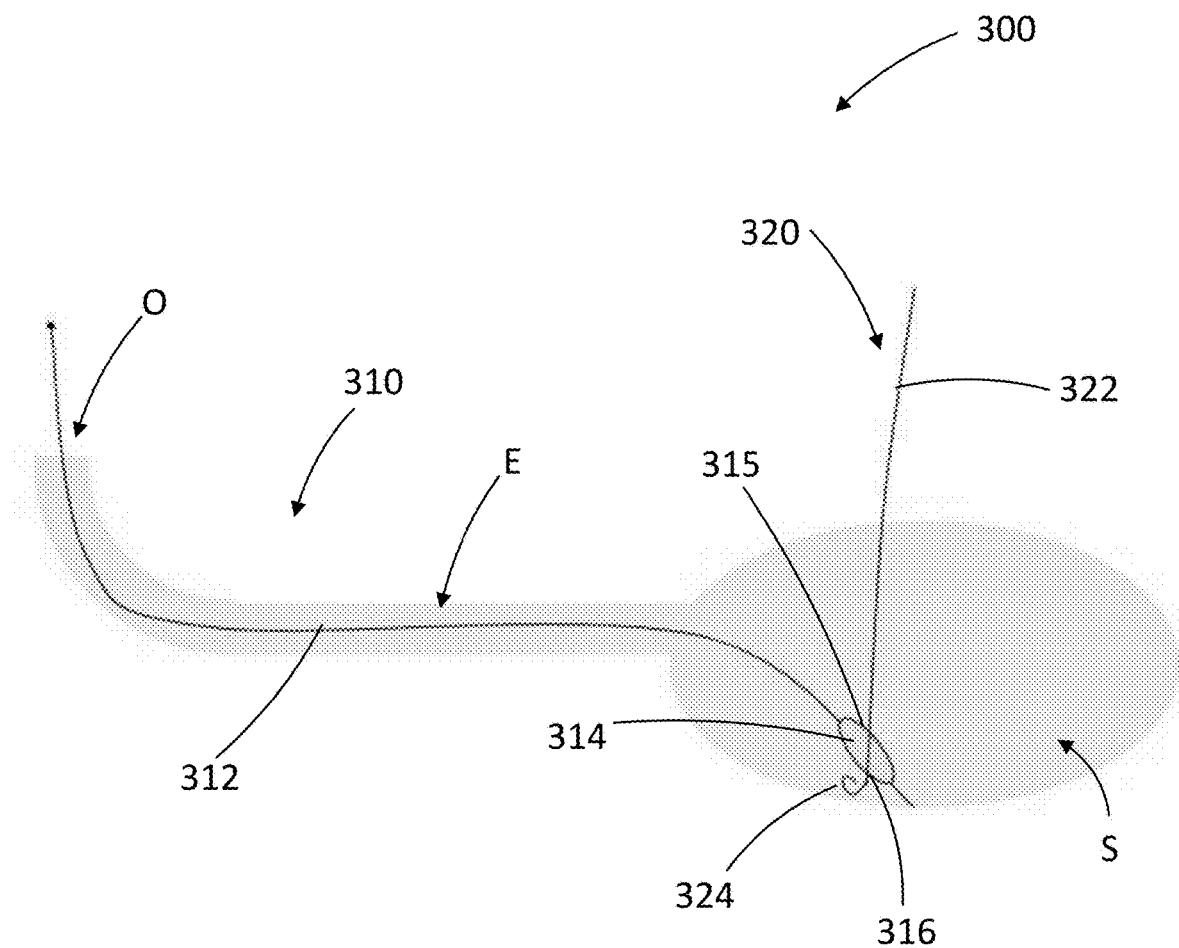
FIG. 17 is a schematic illustration of the system of FIG. 15, with the needle removed and the guidewire assembly extending through the inflatable member.

Although the system 300 shows the coupling member 324 disposed within the interior of the inflatable member 314, in some embodiments the coupling member 324 can be disposed outside of the inflatable member 314 and coupled to an outer surface of the inflatable member 314 when the coupling member 324 and the inflatable member 314 are coupled to each other. For example, as shown in FIG. 15, the needle 330 can pass through a first sidewall portion and a second oppositely disposed sidewall portion such that the first end 331 of the needle 330 is disposed outside of the inflatable member 314 and the needle 330 has created two access orifices in the inflatable member 314. As shown in FIG. 16, the coupling member 324 can then be extended beyond the first end of the needle 330 such that the coupling member 324 is disposed outside of the inflatable member 314. As shown in FIG. 17, the needle 330 can then be withdrawn relative to the coupling member 324 such that the guidewire 322 attached to the coupling member 324 remains disposed within the two access orifices in the inflatable member 314 and the coupling member 324 is engageable with the outer surface of the inflatable member 314.

Figure 18:
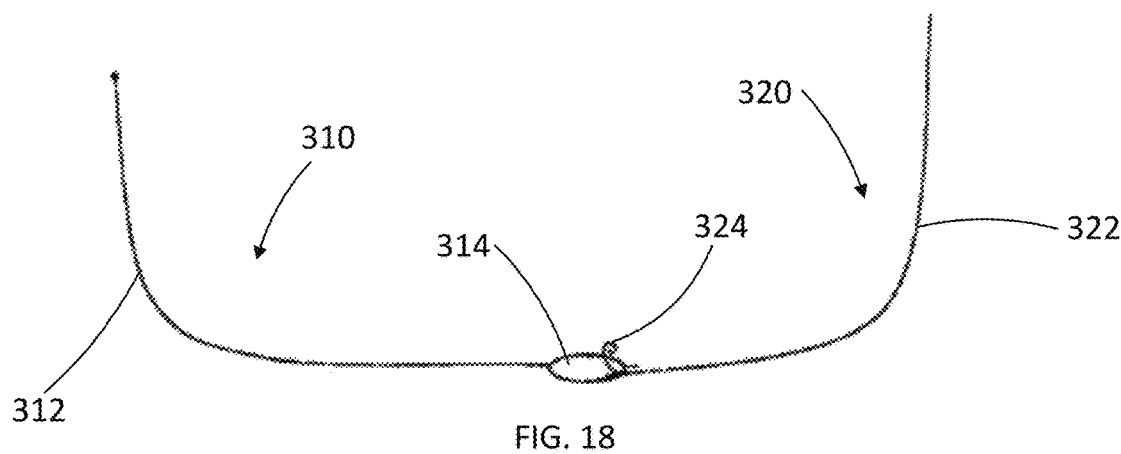
FIG. 18 is a schematic illustration of the system of FIG. 15, with the inflation assembly translating the guidewire assembly.
Figure 19:
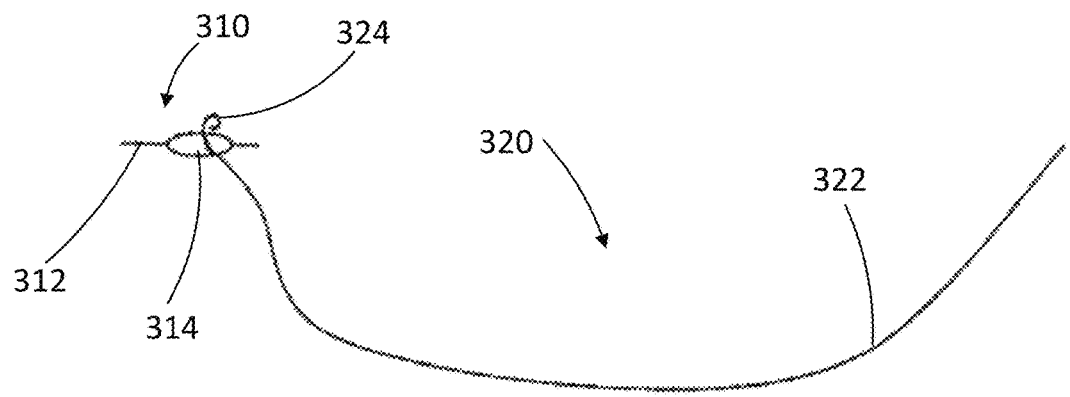
FIG. 19 is a schematic illustration of the system of FIG. 15, with the inflation assembly further translating the guidewire assembly.

As shown in FIG. 18, the inflation assembly 310 can be translated (e.g., through the esophagus) such that the coupling member 324 and the guidewire 322 are translated in the same direction as the inflatable member 314, similarly as described with respect to FIG. 9. As shown in FIG. 19, the inflation assembly 310 can be further translated out of a patient orifice (e.g., out of an orifice such as the mouth of a patient) such that the coupling member 324 is also translated out of the orifice and such that the guidewire 322 extends through the orifice, through a route within the patient, and out of another orifice of the patient (such as an orifice in the patient's stomach wall).

Figure 20A:
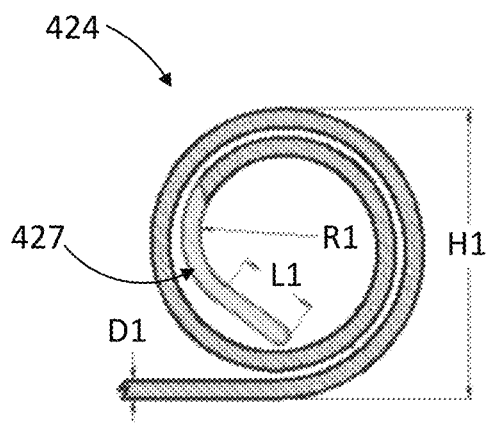
FIGS. 20A-20D are schematic illustrations of various coupling member pigtail configurations, according to various embodiments.

In some embodiments, the guidewire assembly can have any suitable shape and size. In some embodiments, the shape of a coupling member (e.g., a pigtail) can depend, at least in part, on the diameter of the wire forming the coupling member 724 and the number of turns. In some embodiments, these can be selected based on the intended application (e.g., gastrostomy) and/or on the amount of space available within the anatomy for the engagement of the coupling member with an inflatable member and for translation of the inflatable member and the coupling member. In some embodiments, the coupling member of a guidewire assembly can take any suitable number of turns. For example, FIGS. 20A-20D are examples of coupling members having pigtail shapes including various turn shapes. FIG. 20A shows a coupling member 424 including a two-turn pigtail. The coupling member 424 can include a distal end portion 427. The coupling member 424 can have a diameter D1 of, for example, about 0.030 inches. The coupling member 424 can have a distance H1 from a first end to a second end of the outermost turn of, for example, about 0.477 inches. The distal end portion 427 can include a straight distal end portion having a length L1 and a curved portion having a radius of curvature of R1. The length L1 can be, for example, about 0.129 inches, and the radius of curvature R1 can be, for example, about 0.110 inches.

Figure 20B:
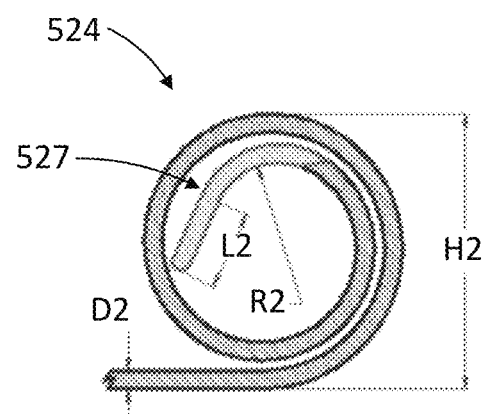

FIG. 20B shows a coupling member 524 including a 1.75-turn pigtail. The coupling member 524 can include a distal end portion 527. The coupling member 524 can have a diameter D2 of, for example, about 0.129 inches. The coupling member 524 can have a distance H2 from a first end to a second end of the outermost turn of, for example, 0.453 inches. The distal end portion 527 can include a straight distal end portion having a length L2 and a curved portion having a radius of curvature of R2. The length L2 can be, for example, about 0.129 inches, and the radius of curvature R2 can be, for example, about 0.110 inches.

Figure 20C:
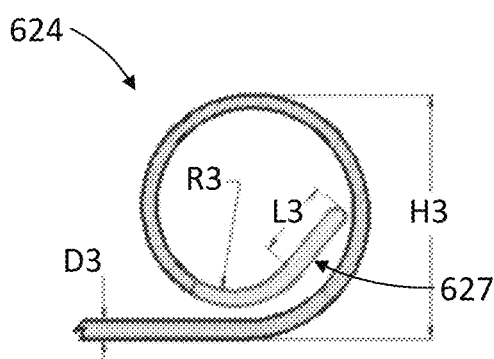

FIG. 20C shows a coupling member 624 including a 1.25-turn pigtail. The coupling member 624 can include a distal end portion 627. The coupling member 624 can have a diameter D3 of, for example, 0.030 inches. The coupling member 624 can have a distance H3 from a first end to a second end of the outermost turn of, for example, 0.402 inches. The distal end portion 627 can include a straight distal end portion having a length L3 and a curved portion having a radius of curvature of R3. The length L3 can be, for example, about 0.129 inches, and the radius of curvature R3 can be, for example, about 0.110 inches.

Figure 20D:
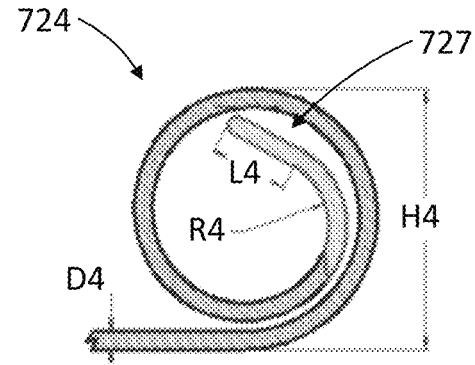

FIG. 20D shows a coupling member 724 including a 1.5-turn pigtail. The coupling member 724 can include a distal end portion 727. The coupling member 724 can have a diameter D4 of, for example, 0.030 inches. The coupling member 724 can have a distance H4 from a first end to a second end of the outermost turn of, for example, 0.420 inches. The distal end portion 727 can include a straight distal end portion having a length L4 and a curved portion having a radius of curvature of R4. The length L4 can be, for example, about 0.129 inches, and the radius of curvature R4 can be, for example, about 0.110 inches.

Figure 21A:
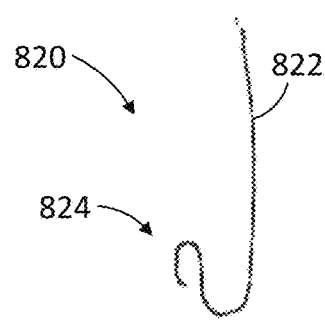
FIGS. 21A-21F are schematic illustrations of various two-dimensional coupling member configurations, according to various embodiments.
Figure 21B:
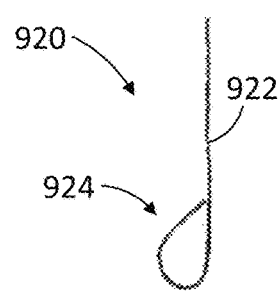
Figure 21C:
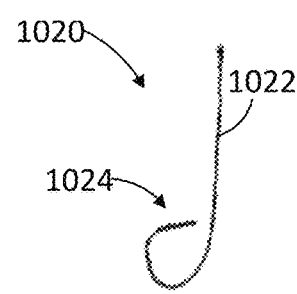
Figure 21D:
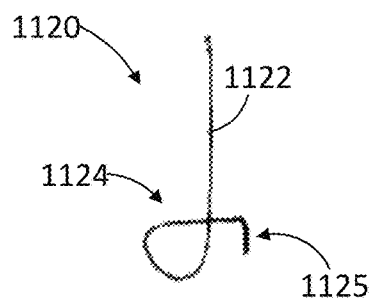
Figure 21E:
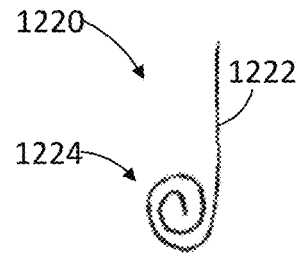
Figure 21F:
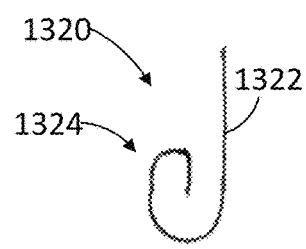

Similarly as shown and described with respect to the pigtail shape, any of the coupling members described herein can include corkscrews of various numbers of turns or hooks of various shapes. For example, FIGS. 21A-21F show a number of possible two dimensional guidewire assembly shapes. Each of the guidewire assemblies shown in FIGS. 21A-21F can be included in any of the systems or methods described herein. For example, FIG. 21A shows a guidewire assembly 820 including a guidewire 822 and a coupling member 824. The coupling member 824 has a first hook-shaped portion and a second hook-shaped portion oppositely oriented in an S-shape. FIG. 21B shows a guidewire assembly 920 including a guidewire 922 and a coupling member 924. The coupling member 924 is shaped as a loop such that the end of the coupling member 924 is adjacent or nearly adjacent a portion of the guidewire 922. FIG. 21C shows a guidewire assembly 1020 including a guidewire 1022 and a coupling member 1024. The coupling member 1024 is shaped as a partial loop relative to the guidewire 1022. FIG. 21D shows a guidewire assembly 1120 including a guidewire 1122 and a coupling member 1124. The coupling member 1124 can be shaped as a loop such that a first portion of the coupling member 1124 overlaps a second portion of the coupling member 1124. The coupling member 1124 can include an end portion 1125 that is disposed substantially perpendicular to the first portion of the coupling member 1124 to which the end portion 1125 is coupled. FIG. 21E shows a guidewire assembly 1220 having a guidewire 1222 and a coupling member 1224. The coupling member 1224 is shaped as a two-turn pigtail. FIG. 21F shows a guidewire assembly 1320 having a guidewire 1322 and a coupling member 1324. The coupling member 1324 is shaped as a one-turn pigtail. The end portion of the coupling member 1324 may be spaced from the guidewire 1322 by a distance. For example, the distance between the end portion of the coupling member 1324 and the guidewire 1322 to which the coupling member 1324 is coupled may be about half a width of the coupling member 1324.

Figure 22:
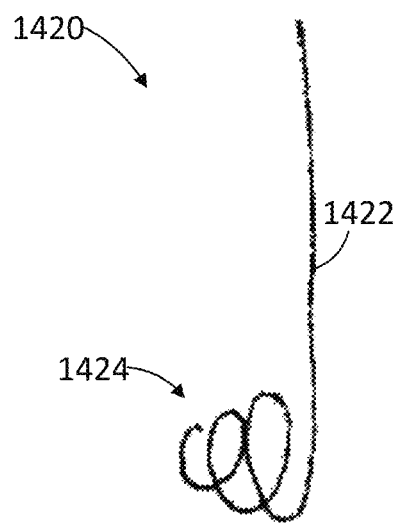
FIG. 22 is a schematic illustration of a three-dimensional coupling member, according to an embodiment.

In some embodiments, the coupling members can have any suitable three-dimensional shape. For example, FIG. 22 shows a guidewire assembly 1420 including a guidewire 1422 and a coupling member 1424. As shown, the coupling member 1424 can have a spiral configuration (e.g., a conic spiral configuration). In some embodiments, the coupling member 1424 can have a helix configuration.

Figure 23:
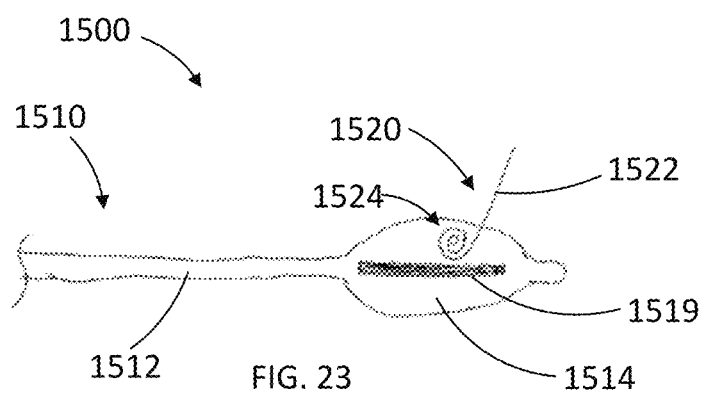
FIGS. 23-26 are schematic illustrations of various inflation assembly and guidewire assembly engagement configurations, according to various embodiments.

In some embodiments, an inflation assembly, such as any of the inflation assemblies described herein, can include a barrier within an inflatable member such that a coupling member can be engaged with the inflatable member between the barrier and an inner surface of the inflatable member. For example, FIG. 23 is an illustration of a system 1500. The system 1500 can be the same or similar in structure and/or function to any of the systems described herein. The system 1500 includes an inflation assembly 1510 and a guidewire assembly 1520. The inflation assembly 1510 can include an elongated tube 1512 and an inflatable member 1514. A barrier 1519 can be included within the inflatable member 1514. The guidewire assembly 1520 can include a guidewire 1522 and a coupling member 1524. As shown in FIG. 23, the coupling member 1524 can be engaged with the inflatable member 1514 such that the coupling member 1524 is retained between the barrier 1519 and the inner surface of the inflatable member 1514. In some embodiments, the barrier 1519 can prevent the coupling member 1524 from passing all the way through the inflatable member 1514. In some embodiments, the barrier 1519 can be coupled to the elongated tube 1512.

Figure 24:
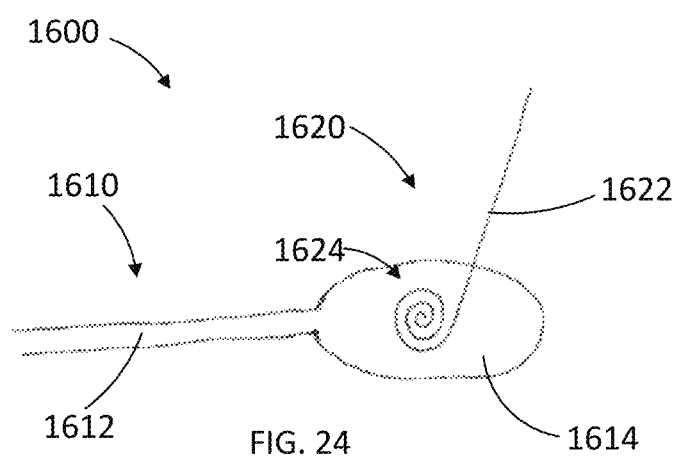

In some embodiments, a system, such as any of the inflation assemblies described herein, can be configured such that a coupling member of a guidewire assembly can be inserted into the interior of an inflatable member of an inflation assembly and retained within the interior of the inflatable member by an inner surface of a wall of the inflatable member. For example, FIG. 24 is an illustration of a system 1600. The system 1600 can be the same or similar in structure and/or function to any of the systems described herein. The system 1600 includes an inflation assembly 1610 and a guidewire assembly 1620. The inflation assembly 1610 can include an elongated tube 1612 and an inflatable member 1614. The guidewire assembly 1620 can include a guidewire 1622 and a coupling member 1624. The coupling member 1624 can be formed as a pigtail with any suitable number of turns, such as, for example, three. As shown in FIG. 24, the coupling member 1624 can be engaged with the inflatable member 1614 such that the coupling member 1624 is retained within the interior of the inflatable member 1614 by an inner surface of a wall of the inflatable member 1614.

Figure 25:
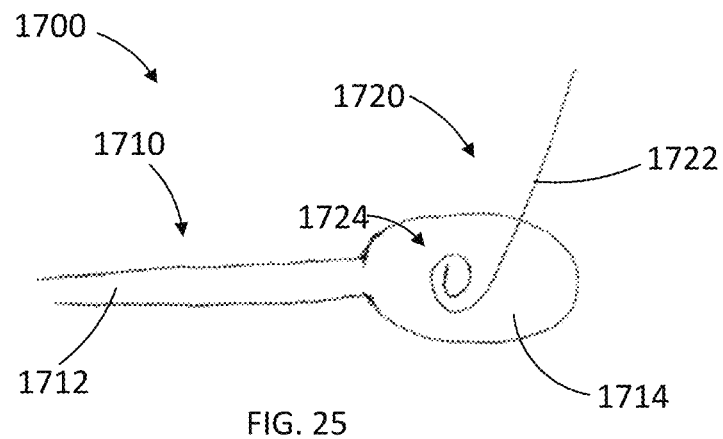

In some embodiments, a system, such as any of the inflation assemblies described herein, can be configured such that a coupling member of a guidewire assembly includes only 1.5 turns. For example, FIG. 25 is an illustration of a system 1700. The system 1700 can be the same or similar in structure and/or function to any of the systems described herein. The system 1700 includes an inflation assembly 1710 and a guidewire assembly 1720. The inflation assembly 1710 can include an elongated tube 1712 and an inflatable member 1714. The guidewire assembly 1720 can include a guidewire 1722 and a coupling member 1724. As shown in FIG. 25, the coupling member 1724 can be formed as a pigtail with 1.5 turns. The coupling member 1724 can be engaged with the inflatable member 1714 such that the coupling member 1724 is retained within the interior of the inflatable member 1714 by an inner surface of a wall of the inflatable member 1714.

Figure 26:
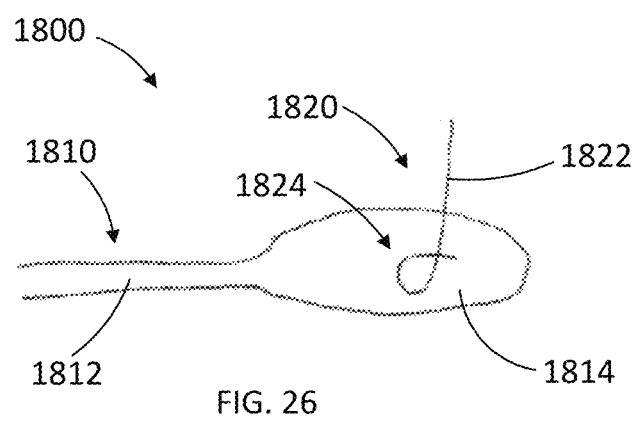

In some embodiments, a system, such as any of the inflation assemblies described herein, can be configured such that a coupling member of a guidewire assembly includes a loop shape. For example, FIG. 26 is an illustration of a system 1800. The system 1800 can be the same or similar in structure and/or function to any of the systems described herein. The system 1800 includes an inflation assembly 1810 and a guidewire assembly 1820. The inflation assembly 1810 can include an elongated tube 1812 and an inflatable member 1814. The guidewire assembly 1820 can include a guidewire 1822 and a coupling member 1824. As shown in FIG. 26, the coupling member 1824 can be formed as a loop. The coupling member 1824 can be engaged with the inflatable member 1814 such that the coupling member 1824 is retained within the interior of the inflatable member 1814 by an inner surface of a wall of the inflatable member 1814.

Figure 27:
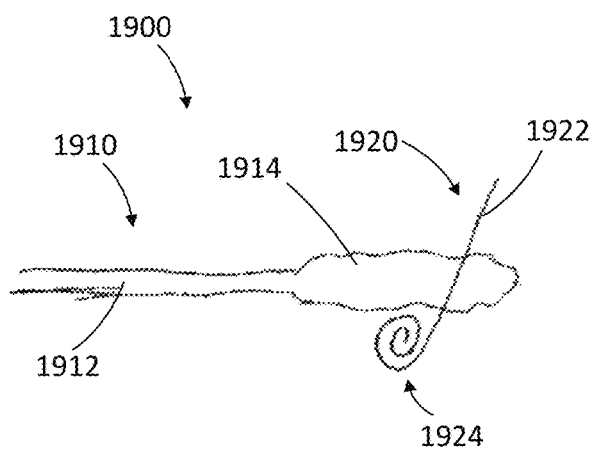
FIG. 27 is a schematic illustration of an inflation assembly engaged with a guidewire assembly in a first inflation state, according to an embodiment.

In some embodiments, the inflatable member can be deflated after engagement with the coupling member and prior to translation of the inflatable member and coupling member out of the patient's body. For example, FIG. 27 is an illustration of a system 1900 in a first inflation state. The system 1900 can be the same or similar in structure and/or function to any of the systems described herein. For example, the system 1900 can include an inflation assembly 1920 including an elongated tube 1912 and an inflatable member 1914. The system 1900 can also include a guidewire assembly 1920 including a guidewire 1922 and a coupling member 1924. As shown, the coupling member 1924 can be engaged with the inflatable member 1914 such that the coupling member 1924 is disposed with the outer surface of the inflatable member 1914 and the guidewire 1922 passes through two access orifices in the inflatable member 314. The inflatable member 1914 can be partially deflated (e.g., the fluid can be withdrawn via an inflation lumen).

Figure 28:
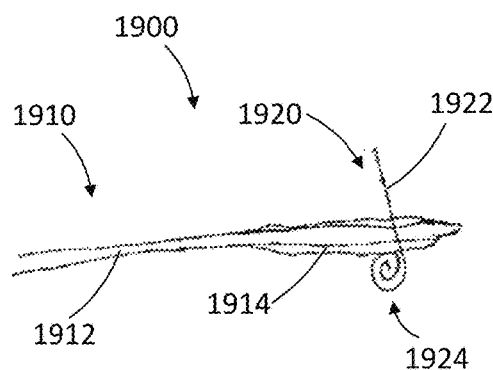
FIG. 28 is a schematic illustration of the inflation assembly and the guidewire assembly of FIG. 27 in a second inflation state.

As shown in FIG. 28, which is an illustration of the system 1900 in a second inflation state, the inflatable member 1914 can be further deflated. The coupling member 1924 can be engaged with the outer surface of the inflatable member 1914 such that movement of the inflatable member 1914 (e.g., via movement of the elongated tube 1912) causes the coupling member 1924 to move similarly.

Although the systems and methods described herein are described in relation to disposing a feeding or gastrostomy tube in a patient, the systems and methods can be used for any suitable procedure. For example, the systems described herein can be used for other procedures in which the creation of an access opening is needed. In some embodiments, a method can include translating an inflatable member of an elongated tube through an orifice of a patient and to a first location within the patient. The inflatable member can be the same or similar in structure and/or function to any of the inflatable members described herein. Fluid can then be provided to the inflatable member via a lumen of the elongated tube such that the inflatable member transitions from an uninflated configuration to an inflated configuration. A coupling member of a guidewire assembly, such as any of the guidewire assemblies described herein, can be translated through a tissue wall of the patient to a second location within the patient near the first location. The guidewire assembly can include a guidewire having a first end coupled to the coupling member and a second end disposed outside the patient. The guidewire can extend through the tissue wall when the coupling member is disposed in the second location. The coupling member can then be coupled to the inflatable member. The elongated tube can then be withdrawn through the orifice such that the coupling member and the first end of the guidewire are withdrawn from the orifice and such that the guidewire extends through the orifice, the first location, and the tissue wall of the patient and the second end of the guidewire is disposed outside of the patient.

In some embodiments, a system such as any of the systems described herein can be used for a percutaneous cystostomy. For example, an inflation assembly such as any of the inflation assemblies described herein can be inserted through the urethra and a guidewire assembly such as any of the guidewire assemblies described herein can be inserted through a patient's bladder wall such that a coupling member of the guidewire assembly can be engaged with an inflatable member of the inflation assembly. The inflatable member can then be withdrawn through the urethra such that the coupling member of the guidewire assembly is also withdrawn through the urethra. The guidewire assembly can then extend through the urethra, through the bladder, and out of the patient through the bladder wall. In some embodiments, a system such as any of the systems described herein can be used for a percutaneous tracheostomy.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. A method, comprising:
    translating an inflatable member of an elongated tube through an orifice of a patient, through an esophagus of the patient, and into a stomach of the patient;
    inflating the inflatable member via a lumen of the elongated tube such that the inflatable member transitions from an uninflated configuration to an inflated configuration;
    inserting a first end of a needle through a stomach wall of the stomach and through a sidewall of the inflatable member;
    translating a coupling member of a guidewire assembly through the stomach wall of the stomach at least partially through a lumen of the needle, the guidewire assembly including a guidewire having a first end coupled to the coupling member and a second end disposed outside the patient, the guidewire extending through the stomach wall;
    coupling the coupling member to the inflatable member; and
    withdrawing the elongated tube through the orifice such that the coupling member and the first end of the guidewire are withdrawn from the orifice and such that the guidewire extends through the esophagus, stomach, and stomach wall of the patient and the second end of the guidewire is disposed outside of the patient.

2. The method of claim 1, further comprising visualizing the location of the inflatable member via ultrasound.

3. The method of claim 1, wherein inflating the inflatable member includes providing a fluid including a contrast medium to the inflatable member, and further comprising visualizing the location of the inflatable member via fluoroscopy.

4. The method of claim 1, wherein the sidewall is a first sidewall portion, and further comprising translating the first end of the needle through a second sidewall portion of the inflatable member, the coupling of the coupling member to the inflatable member including translating the coupling member out of the first end of the needle and withdrawing the needle along the guidewire of the guidewire assembly such that the coupling member is disposed outside of the inflatable member and the guidewire extends from the coupling member through the first sidewall portion, through the second sidewall portion, and through the stomach wall.

5. The method of claim 1, wherein the coupling member is configured to transition between a first configuration in which the coupling member is pigtail-shaped and a second configuration in which the coupling member is straight, the coupling member being biased toward the first configuration, the coupling member being retained in the second configuration by the needle when the coupling member is disposed within the lumen of the needle,
    wherein the coupling of the coupling member to the inflatable member includes translating the coupling member beyond the first end of the needle such that the coupling member at least partially transitions from the second configuration to the first configuration and withdrawing the needle relative to the coupling member such that the coupling member is retained by the sidewall of the inflatable member and the guidewire extends from the coupling member, through the sidewall of the inflatable member, and through the stomach wall.

6. The method of claim 1, wherein the inflatable member includes a first magnetic component and the coupling member includes a second magnetic component, the first magnetic component configured to magnetically couple to the second magnetic component such that translation of the elongated tube translates the guidewire assembly.

7. The method of claim 1, further comprising deflating the inflatable member after coupling the coupling member to the inflatable member.

8. The method of claim 1, wherein the orifice of the patient is the nasal orifice.

9. The method of claim 1, wherein the orifice of the patient is the oral orifice.

10. The method of claim 1, further comprising, after withdrawing the elongated tube through the orifice such that the coupling member and the first end of the guidewire are withdrawn from the orifice, decoupling the coupling member and the inflatable member.

11. A method, comprising:
    translating an inflatable member of an elongated tube through an orifice of a patient and to a first location within the patient;
    inflating the inflatable member via a lumen of the elongated tube such that the inflatable member transitions from an uninflated configuration to an inflated configuration;
    inserting a first end of a needle through a tissue wall of the patient and through a sidewall of the inflatable member;
    translating a coupling member of a guidewire assembly through the tissue wall of the patient at least partially through a lumen of the needle to a second location within the patient near the first location, the guidewire assembly including a guidewire having a first end coupled to the coupling member and a second end disposed outside the patient, the guidewire extending through the tissue wall;
    coupling the coupling member to the inflatable member; and
    withdrawing the elongated tube through the orifice such that the coupling member and the first end of the guidewire are withdrawn from the orifice and such that the guidewire extends through the orifice, the first location, and the tissue wall of the patient and the second end of the guidewire is disposed outside of the patient.

12. The method of claim 11, further comprising visualizing the location of the inflatable member via ultrasound.

13. The method of claim 11, wherein inflating the inflatable member includes providing a fluid including a contrast medium to the inflatable member, and further comprising visualizing the location of the inflatable member via fluoroscopy.

14. The method of claim 11, wherein the sidewall is a first sidewall portion, and further comprising translating the first end of the needle through a second sidewall portion of the inflatable member, the coupling of the coupling member to the inflatable member including translating the coupling member out of the first end of the needle and withdrawing the needle along the guidewire of the guidewire assembly such that the coupling member is disposed outside of the inflatable member and the guidewire extends from the coupling member through the first sidewall portion, through the second sidewall portion, and through the tissue wall of the patient.

15. The method of claim 11, wherein the coupling member is configured to transition between a first configuration in which the coupling member is pigtail-shaped and a second configuration in which the coupling member is straight, the coupling member being biased toward the first configuration, the coupling member being retained in the second configuration by the needle when the coupling member is disposed within the lumen of the needle,
wherein the coupling of the coupling member to the inflatable member includes translating the coupling member beyond the first end of the needle such that the coupling member at least partially transitions from the second configuration to the first configuration and withdrawing the needle relative to the coupling member such that the coupling member is retained by the sidewall of the inflatable member and the guidewire extends from the coupling member, through the sidewall of the inflatable member, and through the tissue wall of the patient.

16. The method of claim 11, wherein the inflatable member includes a first magnetic component and the coupling member includes a second magnetic component, the first magnetic component configured to magnetically couple to the second magnetic component such that translation of the elongated tube translates the guidewire assembly.

17. The method of claim 11, further comprising deflating the inflatable member after coupling the coupling member to the inflatable member.

18. The method of claim 11, wherein the orifice of the patient is the nasal orifice.

19. The method of claim 11, wherein the orifice of the patient is the oral orifice.

20. The method of claim 11, further comprising, after withdrawing the elongated tube through the orifice such that the coupling member and the first end of the guidewire are withdrawn from the orifice, decoupling the coupling member and the inflatable member.

* * * * *